(12) United States Patent
Shi et al.

(10) Patent No.: US 7,732,434 B2
(45) Date of Patent: Jun. 8, 2010

(54) MACROCYCLIC ACYL GUANIDINES AS BETA-SECRETASE INHIBITORS

(75) Inventors: Shuhao Shi, Madison, CT (US); Samuel Gerritz, Guilford, CT (US); Shirong Zhu, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 114 days.

(21) Appl. No.: 12/099,334

(22) Filed: Apr. 8, 2008

(65) Prior Publication Data

US 2008/0262055 A1 Oct. 23, 2008

Related U.S. Application Data

(60) Provisional application No. 60/912,938, filed on Apr. 20, 2007.

(51) Int. Cl.
C07D 267/22 (2006.01)
A61K 31/33 (2006.01)

(52) U.S. Cl. .................. 514/183; 514/373; 514/379; 540/456

(58) Field of Classification Search ............. 540/456; 514/183, 373, 379
See application file for complete search history.

(56) References Cited

FOREIGN PATENT DOCUMENTS

| WO | WO 02/100856 | 12/2002 |
| WO | WO 2004/062625 | 7/2004 |
| WO | WO 2005/018545 | 3/2005 |
| WO | WO 2005/049585 | 6/2005 |

OTHER PUBLICATIONS

Cole, D.C., et al., "Acylguanidine as Small-Molecule β-Secretase Inhibitors", *J. Med. Chem.* 49 (2006) 6158-6161.
Ghosh, A. K., et al. "Structure-based design of cycloamide-urethane-derived novel inhibitors of human brain memapsin 2 (β-secretase)", *Bioorganic and Medicinal Chem. Lett.* 15 (2005) 15-20.
Hussain, I. et al. "Identification of a Novel Aspartic Protease (Asp 2) as β-Secretase", *Mol. Cell. Neurosci.* 14 (1999) 419-427.
Lin, X. et al., "Human aspartic protease memapsin 2 cleaves the β-secretase site of β-amyloid precursor protein", *Proceedings of the National Academy of Sciences of the USA* (PNAS) 97 (2000) 1456-1460.
Luo, Yi, et al., "Mice deficient in BACE1, the Alzheimer's β-secretase, have normal phenotype and abolished β-amyloid generation", *Nature Neuroscience* 4 (2001) 231-232.
Roberds, S.L. et al., "BACE knockout mice are healthy despite lacking the primary β-secretase activity in brain: implications for Alzheimer's disease therapeutics", *Human Molecular Genetics* 10 (2001) 1317-1324.

Seiffert, D.; et al., "Presenilin-1 and -2 are molecular targets for γ-secretase inhibitors" *J. Biol. Chem.* 275 (2000) 34086-34091.
Selkoe, D. J., "Biochemical Analyses of Alzheimer's Brain Lesions lead to the Identification of αβ and its Precursor", *Ann. Rev. Cell Biol.* 10 (1994) 373-403.
Selkoe, D. J., "Alzheimer's Disease: Genes, Proteins, and Therapy", *Physiol. Rev.* 81 (2001) 741-766.
Sinha, S., et al., "Purification and cloning of amyloid precursor protein β-secretase from human brain", Nature 402 (1999) 537-540.
Stachel, S.J., et al., "Macrocyclic Inhibitors of β-Secretase: Functional Activity in an Animal Model", J. Med. Chem. 49 (2006) 6147-6150.
Thal, D.R., et al., "Two Types of Sporadic Cerebral Amyloid Angiopathy", J. Neuropath. Exp. Neuro. (2002) 61: 282-293.
Vassar, R., et al., "β-Secretase Cleavage of Alzheimer's Amyloid Precursor Protein by the Transmembrane Aspartic Protease BACE", Science 286 1999) 735-741.
Walsh, D. M., et al., "Amyloid-β oligomers: their production, toxicity and therapeutic inhibition", . Biochemical Society Transactions 30 (2002) 552-557.
Wolfe, M. J., "Secretase Targets for Alzheimer's Disease: Identification and Therapeutic Potential", J. Med. Chem. 44 (2001) 2039-2060.
Yan, R., et al., "Membrane-anchored aspartyl protease with Alzheimer's disease β-secretase activity", Nature 402 (1999) 533-537.

*Primary Examiner*—Bruck Kifle
(74) *Attorney, Agent, or Firm*—John F. Levis; Aldo A. Algieri

(57) ABSTRACT

There is provided a series of heterocyclic-containing macrocyclic acyl guanidines of Formula (I) or a stereoisomer; or a nontoxic pharmaceutically acceptable salt thereof,

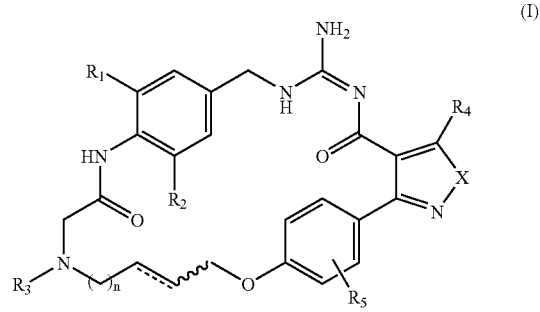

wherein $R_1$, $R_2$, $R_3$, $R_4$, $R_5$, n and X as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

5 Claims, No Drawings

MACROCYCLIC ACYL GUANIDINES AS BETA-SECRETASE INHIBITORS

CROSS REFERENCE

This is a non-provisional application which claims the benefit of U.S. Provisional Application Ser. No. 60/912,938 filed Apr. 20, 2007.

FIELD OF THE DISCLOSURE

This patent application provides heterocyclic-containing macrocyclic acyl guanidines compounds having drug and bio-affecting properties, their pharmaceutical compositions and method of use. In particular, the disclosure is concerned with a series of novel heterocyclic-containing macrocyclic acyl guanidines which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.* 1994, 10, 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing Aβ levels is to interfere with the action of the secretases that are directly involved in the cleavage of APP to Aβ. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., *Mol. Cell. Neurosci.*, 1999, 14, 419-427; Lin, X. et al., *Proceedings of the National Academy of Sciences of the United States of America* 2000, 97: 1456-1460; Sinha, S., et al., *Nature* 1999, 402, 537-540; Vassar, R., et al., *Science* 1999, 286, 735-741; Walsh, D. M., et al., *Biochemical Transactions* 2002, 30, 552-557; Wolfe, M. *J. Med. Chem.* 2001, 44, 2039-2060; Yan, R. et al., *Nature* 1999, 402, 533-537].

Removal of BACE activity in mice by gene targeting completely abolishes Aβ production [see Luo, Y., et al., *Nature Neuroscience* 2001, 4, 231-232; Roberds, S. L., et al., *Human Molecular Genetics* 2001, 10, 1317-1324]. BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2005049585, published Jun. 2, 2005 discloses novel macrocyclic lactams for the treatment of neurological and vascular disorders related to β-amyloid generation and/or aggregation.

PCT Publication WO 2005018545 A2, published Mar. 3, 2005 discloses macrocyclic BACE inhibitors for the treatment of Alzheimers.

Published article Ghosh, A. K. et al., *Bioorganic and Medicinal Chem. Lett.* 2005, 15, 15-20 discloses macrocyclic amide-urethane inhibitors of BACE.

PCT Publication WO 2004062625 A2, published Jul. 29, 2004 discloses macrocyclic BACE inhibitors for the treatment of Alzheimers.

PCT Publication WO 2002100856 A1, published Dec. 19, 2002 discloses macrocycles useful in the treatment of Alzheimers.

Published article Stachel, S. J., et al., *J. Med. Chem.* 2006, 49, 6147-6150 discloses macrocyclic inhibitors of BACE for the treatment of Alzheimers.

Published article Cole, D. C., et al., *J. Med. Chem.* 2006, 49, 6158-6161 discloses acylguanidines inhibitors of BACE 1 for the treatment of Alzheimers.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of heterocyclic-containing macrocyclic acyl guanidines having the Formula (I)

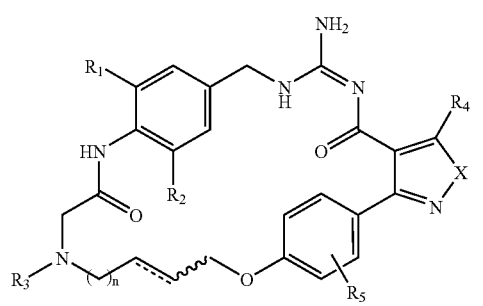

(I)

or a stereoisomer; or a nontoxic pharmaceutically acceptable salt thereof, wherein $R_1$, $R_2$, $R_3$, $R_4$, $R_5$, n and X as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and nontoxic pharmaceutically acceptable salts thereof have the following formula and meanings:

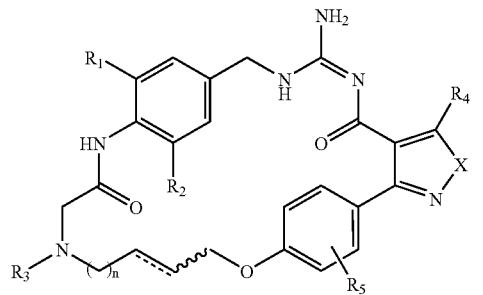

(I)

wherein

= represents a single or double bond;

$R_1$ and $R_2$ are independently hydrogen, halogen, $C_{1-4}$alkyl or $CF_3$;

$R_3$ is hydrogen, $C_{1-4}$alkyl, fluoro $C_{1-4}$alkyl, $CF_3$ or benzyl;

$R_4$ is hydrogen, $C_{1-4}$alkyl or phenyl in which each is optionally substituted with halogen, $C_{1-4}$alkyl or $C_{1-4}$alkoxy;

$R_5$ is hydrogen, halogen, $CF_3$, OH, $NH_2$, $C_{1-4}$alkyl or $C_{1-4}$alkoxy;

n is an integer of 1, 2, 3 or 4; and

X is O or S.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a nontoxic pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Dingwall, C. *Journal of Clinical Investigation* 2001, 108, 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

As used herein and in the claims, "alkyl" or "alkylene" is intended to include both branched and straight-chain saturated aliphatic hydrocarbon groups having the specified number of carbon atoms; for example, "$C_{1-4}$ alkyl" denotes alkyl having 1 to 4 carbon atoms. Examples of alkyl include, but are not limited to, methyl, ethyl, n-propyl, i-propyl, n-butyl, i-butyl, sec-butyl, t-butyl. Preferred "alkyl" group, unless otherwise specified, is "$C_{1-2}$ alkyl". Additionally, unless otherwise specified, "propyl" denotes n-propyl or i-propyl; "butyl" denotes n-butyl, i-butyl, sec-butyl, or t-butyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

The compounds described herein may have asymmetric centers and geometric isomers of olefins and the like, and all such stable isomers are contemplated in the present invention. Cis and trans geometric isomers of the compounds of the present invention are described and may be isolated as a mixture of isomers or as separated isomeric forms. An embodiment of the geometric isomers is illustrated by the compound of formula Ia.

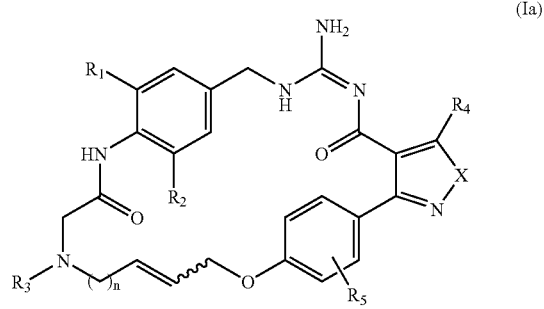

(Ia)

Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns.

All chiral, diastereomeric, racemic forms and all geometric isomeric forms of a structure are intended, unless the specific stereochemistry or isomeric form is specifically indicated.

The phrase "nontoxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Compounds of formula I were prepared as illustrated in Scheme 1. The phenol group of intermediates of formula III may be allylated under standard conditions followed by ester hydrolysis to afford intermediates of formula IV. Intermediates of formula III can be prepared by methods known in the literature, or can be readily prepared by one skilled in the art. Successive treatment of intermediates of formula IV with intermediate of formula V under standard acylating conditions and intermediates of formula VI under standard nucleophilic displacement conditions provides intermediates of formula VII. Intermediate of formula V can be prepared by methods known in the literature, or can be readily prepared by one skilled in the art. Intermediates of formula VI can be prepared by methods known in the literature, or can be readily prepared by one skilled in the art. Intermediates of formula VII are treated with bromoacetylbromide and an organic base to afford intermediates of formula VIII. Intermediates of formula VIII are treated with intermediates of formula IX and an organic base, followed by treatment with BOC anhydride and an organic base to provide intermediates of formula X. Intermediates of formula IX can be obtained from commercial sources, prepared by methods known in the literature, or can be readily prepared by one skilled in the art. Treatment of intermediates of formula X with Grubbs' Second Generation olefin metathesis catalyst affords macrocyclic intermediates of formula XI. Treatment of intermediates of formula XI with trifluoroacetic acid (TFA) and then optionally treated with hydrogen over Pd/C provides compounds of formula Ib which may then be alkylated to provide compounds of formula I.

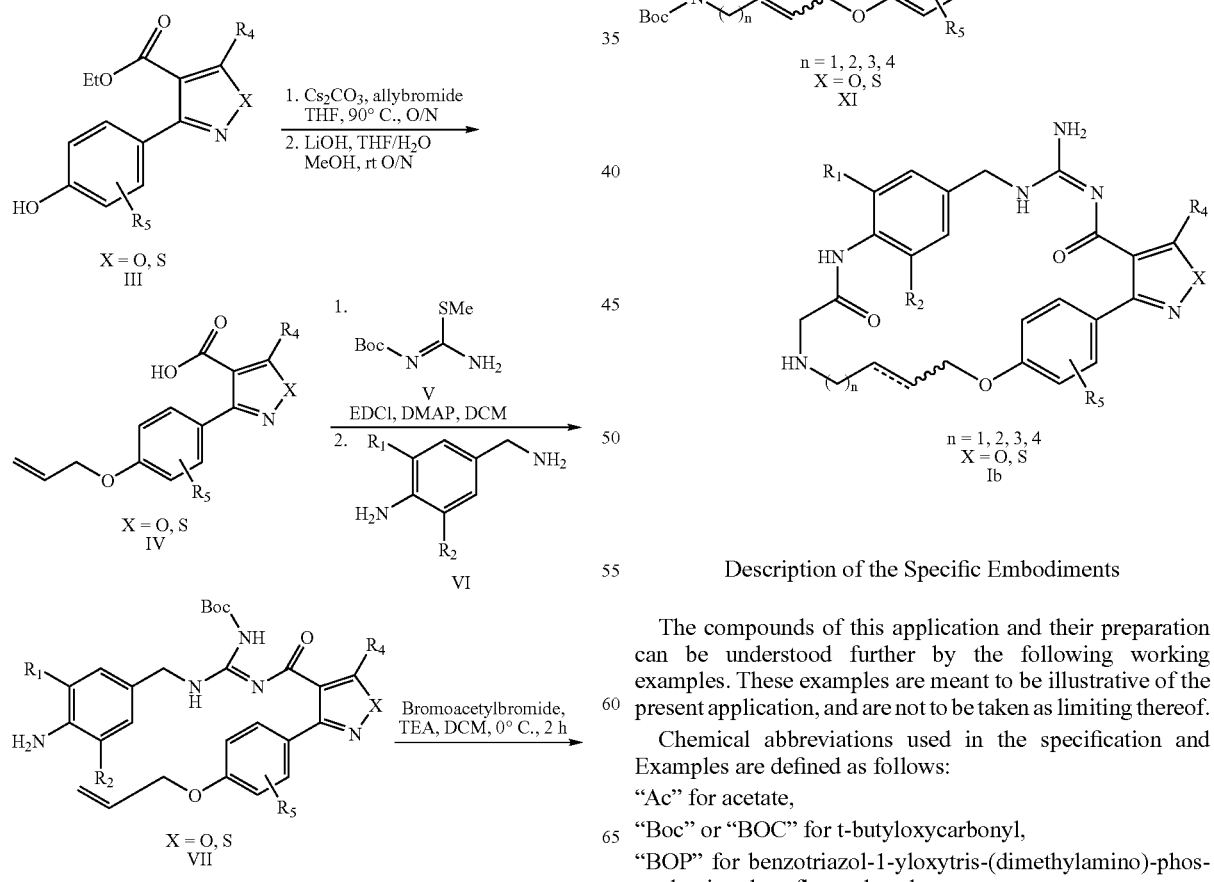

Description of the Specific Embodiments

The compounds of this application and their preparation can be understood further by the following working examples. These examples are meant to be illustrative of the present application, and are not to be taken as limiting thereof.

Chemical abbreviations used in the specification and Examples are defined as follows:

"Ac" for acetate,

"Boc" or "BOC" for t-butyloxycarbonyl,

"BOP" for benzotriazol-1-yloxytris-(dimethylamino)-phosphonium hexafluorophosphate, "Cbz" for benzyloxycarbonyl,
"CDCl₃" for deuterochloroform,
"DCM" for dichloromethane
"DIEA", "Hunig's base", or "DIPEA" for N,N-diisopropylethylamine,
"DME" for 1,2-dimethoxyethane,
"DMF" for N,N-dimethylformamide,
"DMAP" for 4-dimethylaminopyridine,
"DMSO" for dimethylsulfoxide,
"EDC" or "EDCI" for 1-(3-dimethylaminopropyl)-3-ethylcarbodiimide hydrochloride,
"Et" for ethyl,
"EtOAc" for ethyl acetate,
"HOAc" for acetic acid,
"HOBt" for 1-hydroxybenzotriazole hydrate,
"HATU" for O-(7-azabenzotriazol-1-yl)-N, N, N', N'-tetramethyluronium hexafluorophosphate,
"LDA" for lithium diisopropylamide,
"LiHMDS" for lithium bis(trimethylsilyl)amide,
"n-BuLi" for n-butyllithium,
"NMM" for 4-methylmorpholine,
"PyBOP" for benzotriazole-1-yl-oxy-tris-pyrrolidino-phosphonium hexafluorophosphate,
"TBTU" for O-(1H-benzotriazol-1-yl)-N,N,N',N'-tetramethyluronium tetrafluoroborate,
"TEA" for triethylamine,
"TES" for triethylsilane,
"TFA" for trifluoroacetic acid, and
"THF" for tetrahydrofuran.

Abbreviations used in the Examples are defined as follows: "C" for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "LC-MS conditions", the conditions described below in Method A, B or C were utilized as indicated.

| LC/MS Method A | |
|---|---|
| Column | XTERRA 3.0 × 50 mm S7 |
| Flow Rate | 4.0 mL/min |
| Solvent A | 5% Acetonitrile - 95% water - 10 mM NH₄OAc |
| Solvent B | 95% Acetonitrile - 5% water - 10 mM NH₄OAc |
| Gradient | % B 0-100 |
| Gradient Time | 3 min. |
| Ionization | positive/negative ions |

| LC/MS Method B | |
|---|---|
| Column | XTERRA 4.6 × 30 mm S5 |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 3 min. |

| LC/MS Method C | |
|---|---|
| Column | PHENOMENEX 4.6 × 30 mm S5 |
| Flow Rate | 4 mL/min |
| Solvent A | 10% MeOH - 90% water - 0.1% TFA |
| Solvent B | 90% MeOH - 10% water - 0.1% TFA |
| Gradient | % B 0-100 |
| Gradient Time | 3 min. |

Proton NMR spectra (referenced to tetramethylsilane) were obtained on a Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

The examples provided are intended to assist in a further understanding of the present disclosure. Particular materials employed, species and conditions are intended to further illustrate the specific embodiments of the invention and not limit the reasonable scope thereof.

Synthesis of Intermediates

Preparation A tert-Butyl methylthiocarbonoimidoylcarbamate

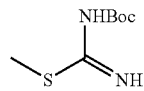

To a rapidly stirred suspension of S-methylisothiourea hemisulfate (60.8 g, 0.437 mol) in CH₂Cl₂ (600 mL) was added 2N NaOH (300 mL, 0.6 mol). This was cooled to 0° C. on an ice bath, and a solution of di-tert-butyl dicarbonate (43.2 g, 0.198 mol) was added dropwise over 6 h. Upon completion of the addition, the mixture was stirred an additional 20 min, diluted with 1L CH₂Cl₂ and the phases were separated. The organic portion was washed with water (2×500 ml) and dried over Na₂SO₄. Filtration and concentra-

Preparation B

3,5-Dichloro-4-aminobenzylamine

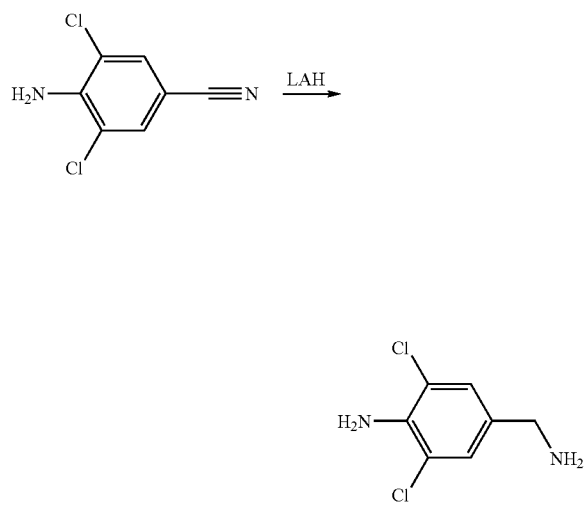

To lithium aluminum hydride (0.57 g, 15 mmol) in dry THF (20 mL) was added dropwise 3,5-dichloro-4-aminobenzonitrile (1.87 g, 10 mmol) in THF (30 mL). The mixture was stirred at RT for 2 hours. Then, sodium sulfate decahydrate (4.83 g, 15 mmol) was added and stirred for 30 min. The solid was filtered off and washed with THF for three times. The solvent was removed by rotovap and residue was purified by column with Methanol/DCM (3:7) as the eluant. 3,5-dichloro-4-aminobenzylamine was obtained as an off-white solid (1.5 g, 80%). $^1$H NMR (300 MHz, CD$_3$OD): δ 7.2 (s, 2H), 3.65 (s, 2H).

Preparation C

Ethyl 3-(4-hydroxyphenyl)-5-methylisoxazole-4-carboxylate

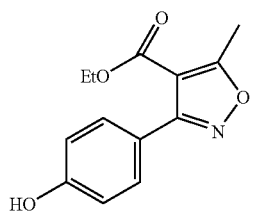

$^1$H NMR (500 MHz, CDCl$_3$) δ 7.52 (d, J=8.7Hz, 2H), 6.86 (d, J=8.7Hz, 2H), 4.26 (q, J=7.2Hz, 2H), 2.71 (s, 3H), 1.26 (t, J=7.2Hz, 3H).

tion provided the desired mono-N-Boc-S-methylisothiourea as a white solid (35.5 g, 0.187 mol, 94% yield based on Boc$_2$O).

Preparation D

Ethyl 3-(4-(allyloxy)phenyl)-5-methylisoxazole-4-carboxylate

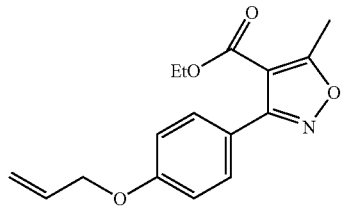

The mixture of ethyl 3-(4-hydroxyphenyl)-5-methylisoxazole-4-carboxylate (Preparation C) (0.474 g, 1.92 mmol), Cs$_2$CO$_3$ (0.937 g, 2.88 mmol) and allyl bromide (0.27 mL, 3.12 mmol) in 10 mL of THF was sealed in a 150-mL pressure vessel and stirred at 90° C. overnight. The reaction mixture was cooled to room temperature. Water (150 mL) and ethyl acetate (150 mL) were added to the reaction mixture. Layers were separated and the aqueous layer was extracted with ethyl acetate (150 mL). The combined organic extract was dried over anhydrous sodium sulfate. Solvent was evaporated in vacuo to give 0.66 g of crude product, which was used in the next step without purification. LCMS (method B) RT 3.34 min., MH$^+$288. $^1$H NMR (500 MHz, CDCl$_3$) δ 7.58 (d, J=8.5Hz, 2H), 6.96 (d, J=8.5Hz, 2H), 6.12-6.00 (m, 1H), 5.46-5.26 (m, 2H), 4.58 (d, J=5.2Hz, 2H), 4.25 (q, J=7.2Hz, 2H), 2.71 (s, 3H), 1.25 (t, J=7.2 Hz, 3H).

Preparation E 3-(4-(Allyloxy)phenyl)-5-methylisoxazole-4-carboxylic acid

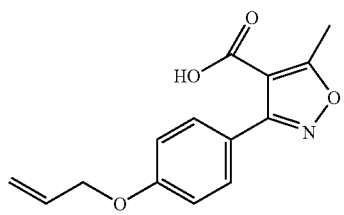

To the crude ethyl 3-(4-(allyloxy)phenyl)-5-methylisoxazole-4-carboxylate (Preparation D) (0.66 g) was added 10 ml of THF, 0.5 mL of water, and 0.240 g of LiOH. The resulted reaction mixture was stirred at room temperature overnight. Water (150 mL) and ethyl acetate (150 mL) were added to the reaction mixture. Layers were separated and the aqueous solution was acidified by addition of 20 mL of 1.4 N HCl. The product was then extracted from the acidic aqueous solution with ethyl acetate (2×150 mL). The combined extract was dried over anhydrous sodium sulfate. Solvent was evaporated to give 0.600 g of product. LCMS (method B) RT 3.00 min., MH$^+$260. $^1$H NMR (500 MHz, CD$_3$OD) δ 7.57 (d, J=8.5Hz, 2H), 6.99 (d, J=8.5Hz, 2H), 6.16-6.01 (m, 1H), 5.45-5.24 (m, 2H), 4.60 (d, J=4.9Hz, 2H), 2.70 (s, 3H).

Preparation F (E)-tert-Butyl N-(3-(4-(allyloxy)phenyl)-5-methylisoxazole-4-carbonyl)(methylthio)carbonoimidoylcarbamate

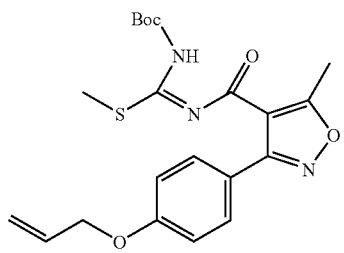

A mixture of tert-butyl methylthiocarbonoimidoylcarbamate (Preparation A) (0.519 g, 2.73 mmol), 3-(4-(allyloxy)phenyl)-5-methylisoxazole-4-carboxylic acid (Preparation E) (0.590 g, 2.28 mmol), EDCI (0.523 g, 2.73 mmol) and DMAP (0.556 g, 4.55 mmol) in DCM (20 mL) was stirred at room temperature for 16 hours. The solvent was concentrated in vacuo and residue was purified by flash chromatography (DCM, Rf 0.43) to give 0.72 g (73%, theoretical yield 0.98 g). LCMS (method B) RT 3.71 min., MH$^+$432. $^1$H NMR (500 MHz, CDCl$_3$) δ 12.32 (s, 1H), 7.48 (d, J=8.7Hz, 2H), 6.96 (d, J=8.7Hz, 2H), 6.11-5.97 (m, 1H), 5.45-5.38 (m, 1H), 5.33-5.27 (m, 1H), 4.57 (d, J=5.2 Hz, 2H), 2.75 (s, 3H), 1.90 (s, 3H), 1.49 (s, 9H).

Preparation G (Z)-tert-Butyl N-(4-amino-3,5-dichlorobenzyl)-N'-(3-(4-(allyloxy)phenyl)-5-methylisoxazole-4-carbonyl)carbamimidoylcarbamate

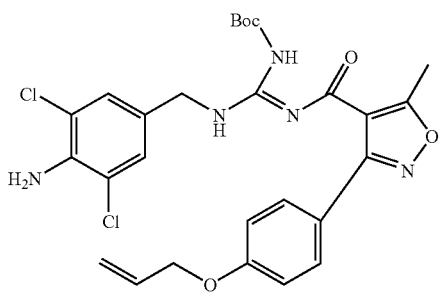

A mixture of (E)-tert-butyl N-(3-(4-(allyloxy)phenyl)-5-methylisoxazole-4-carbonyl)(methylthio)carbonoimidoylcarbamate (Preparation F) (0.390 g, 0.904 mmol), 3,5-dichloro-4-aminobenzylamine (Preparation B) (0.216 g, 1.13 mmol) and DIPEA (0.197 mL, 1.13 mmol) in DCM (20 mL) was stirred overnight. DCM (100 mL) and 0.1 N NaOH aqueous solution (50 mL) were added to the reaction mixture. Layers separated and the aqueous layer was extracted with 100 mL of DCM. The combined DCM solution was dried over anhydrous sodium sulfate. Solvent was evaporated in vacuo to give a crude product, which was purified by flash chromatography (DCM, Rf 0.1) to give 0.420 g (81%, theoretical yield 0.519 g). LCMS (method B) RT 3.90 min., MH$^+$574. $^1$H NMR (CDCl$_3$, 500 MHz) δ 12.17 (s, 1H), 8.65 (s, 1H), 7.51 (d, J=7.9 Hz, 2H), 6.94 (s, 2H), 6.90 (d, J=7.9Hz, 2H), 6.06-5.95 (m, 1H), 5.42-5.33 (m, 1H), 5.28-5.22 (m, 1H), 4.49-4.45 (m, 2H), 4.43 (s, 2H), 4.01 (d, J=5.5 Hz, 2H), 2.71 (s, 3H), 1.47 (s, 9H).

Preparation H (Z)-tert-Butyl N-(4-(2-bromoacetamido)-3,5-dichlorobenzyl)-N'-(3-(4-(allyloxy)phenyl)-5-methylisoxazole-4-carbonyl)carbamimidoylcarbamate

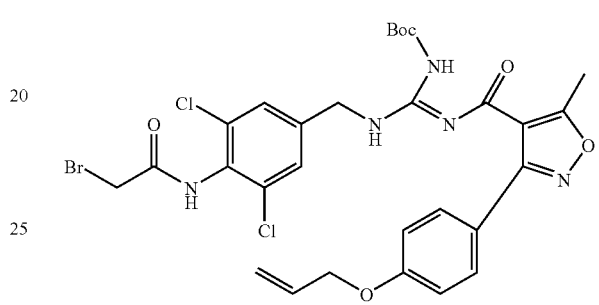

(Z)-tert-Butyl N-(4-amino-3,5-dichlorobenzyl)-N'-(3-(4-(allyloxy)phenyl)-5-methylisoxazole-4-carbonyl)carbamimidoylcarbamate (Preparation G) (0.42 g, 0.731 mmol) was dissolved in 10 mL of anhydrous DCM in a 100-mL round bottom flask, followed by the addition of 0.112 mL (0.804 mmol, 1.1 eq) of triethylamine. The solution was cooled to 0° C. and nitrogen was introduced. Bromoacetyl bromide (0.070 mL, 0.804 mmol, 1.1 eq) was added dropwise and the reaction mixture was stirred at 0° C. for 1 hr. More bromoacetyl bromide (another 0.25 to 1.0 eq depending on the amount of starting material left) was added and the reaction mixture was stirred at 0° C. for 1 to 2 hours. DCM (80 mL) and saturated NaHCO$_3$ aqueous solution (100 mL) were added and the two layers were separated. The aqueous was extracted with DCM (100 mL). The combined DCM solution was dried over anhydrous sodium sulfate. The crude product was purified by flash chromatography (EtOAc/DCM, 5:95, Rf 0.38) to give 0.450 g (95%, theoretical yield 0.508 g) of the compound. LCMS (method C) RT 3.09 min., MH$^+$694 (base peak 696). $^1$H NMR (500 MHz, CDCl$_3$) δ 12.18 (s, 1H), 8.82 (t, J=5.6Hz, 1H), 7.89 (s, 1H), 7.47 (d, J=8.7, 2H), 7.08 (s, 2H), 6.88 (d, J=8.7, 2H), 6.09-5.97 (m, 1H), 5.44-5.36 (m, 1H), 5.32-5.24 (m, 1H), 4.49 (d, J=5.2Hz, 2H), 4.10 (d, J=6.1Hz, 2H), 4.06 (s, 2H), 2.68 (s, 3H), 1.49 (s, 9H).

Preparation I

4-Amino-3-chlorobenzylamine

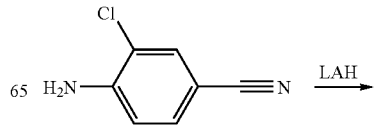

-continued

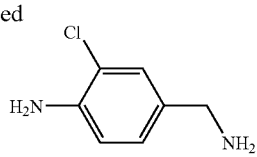

To lithium aluminum hydride (2.11 g, 55.6 mmol) in dry THF (50 mL) was added dropwise 4-amino-3-chlorobenzonitrile (3.29 g, 21.6 mmol) in THF (40 mL). The mixture was stirred at RT for 16 hours. Then, 6.0 mL of 1.0 N NaOH solution was added dropwise and the reaction mixture was stirred for 20 min. The solid was filtered off and washed with THF for three times. The solvent was removed by rotavap to give 4-amino-3-chlorobenzylamine as an oily liquid (3.04 g, 90%). ¹H NMR (500 MHz, CD₃OD): δ 7.18 (d, J=2Hz, 1H), 7.00 (dd, J=8Hz, 2Hz, 1H), 6.78 (d, J=8Hz, 1H), 3.61 (s, 2H).

Preparation J 3-(4-(Allyloxy)phenyl)-5-methylisothiazole-4-carboxylic acid

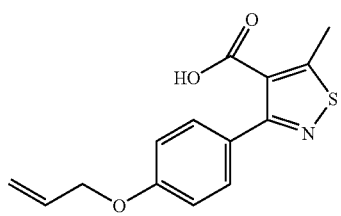

Step J(1): 3-(4-Hydroxyphenyl)-5-methylisothiazole-4-carboxylic acid

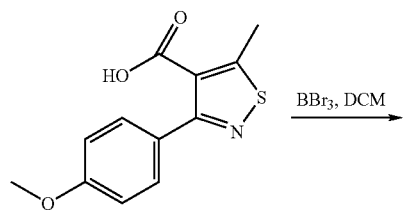

The solution of boron tribromide in dichloromethane (1.0 M, 12.4 mL) in a 100-mL round bottom flask was cooled to −78° C., followed by the addition of 1.03 g of 3-(4-methoxyphenyl)-5-methylisothiazole-4-carboxylic acid as a solid slowly. The reaction mixture was stirred at −78° C. for 2 hrs. and at room temperature overnight. Water (20 mL) was added slowly, followed by the addition of 20 mL of 1.0 N NaOH and 100 mL of dichloromethane. The two layers were separated with a separatory funnel. The aqueous layer was acidified by the addition of concentrated hydrochloric acid. The product was extracted with ethyl acetate (3×100 mL). Solvent was evaporated in vacuo to give 0.935 g of 3-(4-hydroxyphenyl)-5-methylisothiazole-4-carboxylic acid (96%, theoretical yield 0.972 g). LCMS (method B) RT 2.28 min., MH⁺236. ¹H NMR (500 MHz, CD₃OD) δ 7.42 (d, J=8.5Hz, 2H), 6.80 (d, J=8.5Hz, 2H), 2.70 (s, 3H).

Step J(2): 3-(4-(Allyloxy)phenyl)-5-methylisothiazole-4-carboxylic acid

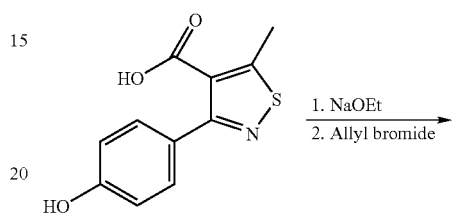

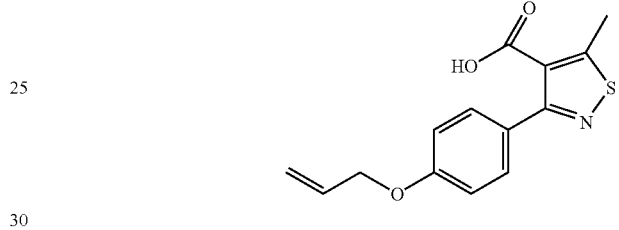

The product (0.916 g, 3.89 mmol) from Step J(1) was dissolved in 15 mL of 200 proof ethyl alcohol, followed by the addition of 7.78 mmol of sodium ethoxide (21% wt. in ethyl alcohol, 2.90 mL). The solution was stirred at room temperature for 1 hr. Allyl bromide (0.337 mL, 3.90 mmol) was added and the reaction mixture was heated at reflux for 5 hrs. The reaction mixture was cooled to RT and concentrated by rotavac. Water (50 mL) and 5% HCl (10 mL) were added. The product was extracted with ethyl acetate (2×150 mL). Solvent was evaporated and the crude product was purified by flash chromatography (MeOH/DCM, 10:90) to give 0.76 g of the title compound 71%, theoretical yield 1.07 g). LCMS (method B) RT 2.94 min., MH⁺276. ¹H NMR (500 MHz, CD₃OD) δ 7.50 (d, J=8.9Hz, 2H), 6.96 (d, J=8.9Hz, 2H), 6.13-6.00 (m, 1H), 5.41 (dd, J=17.1Hz, 1.8Hz, 1H), 5.25 (dd, J=10.7Hz, 1.5Hz, 1H), 4.62-4.55 (m, 1H), 2.71 (s, 3H).

Preparation K

Z)-tert-Butyl N-(4-(2-bromoacetamido)-3,5-dichlorobenzyl)-N'-(3-(4-(allyloxy)phenyl)-5-methylisothiazole-4-carbonyl)carbamimidoylcarbamate

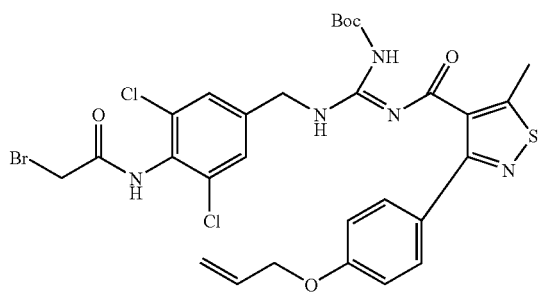

The title compound was prepared from 3-(4-(allyloxy)phenyl)-5-methylisothiazole-4-carboxylic acid (Preparation J) in analogy to the preparation of 5-methylisoxazole-4-carbonyl)carbamimidoylcarbamate (Preparation H) from 3-(4-(allyloxy)phenyl)-5-methylisoxazole-4-carboxylic acid (Preparation E). LCMS (method B) RT 3.66 min., MH+710 (base peak 712). ¹H NMR (500 MHz, CDCl₃) δ 12.11 (s, 1H), 8.77 (t, J=5.8Hz, 1H), 7.93 (s, 1H), 7.45 (d, J=8.7, 2H), 7.09 (s, 2H), 6.85 (d, J=8.7, 2H), 6.09-5.98 (m, 1H), 5.45-5.37 (m, 1H), 5.32-5.25 (m, 1H), 4.49 (d, J=5.2Hz, 2H), 4.04 (s, 2H), 4.00 (d, J=6.1Hz, 2H), 2.66 (s, 3H), 1.51 (s, 9H).

Preparation L (Z)-tert-Butyl N-(4-(2-bromoacetamido)-3-chlorobenzyl)-N'-(3-(4-(allyloxy)phenyl)-5-methylisothiazole-4-carbonyl)carbamimidoylcarbamate

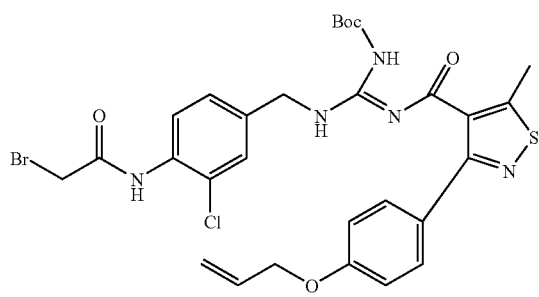

The title compound was prepared by analogy to the protocol for 3-(4-(allyloxy)phenyl)-5-methylisothiazole-4-carboxylic acid (Preparation K), with 4-amino-3-chlorobenzylamine (Preparation I) in place of 3,5-dichloro-4-aminobenzylamine (Preparation B). LCMS (method B) RT 3.46 min., MH+676 (base peak 678). ¹H NMR (500 MHz, CDCl₃) δ 2.11 (s, 1H), 8.73 (s, 1H), 8.69 (t, J=5.2Hz, 1H), 8.25 (d, J=8.4Hz, 1H), 7.48 (d, J=8.9, 2H), 7.15 (d, J=1.8Hz, 1H), 7.03 (dd, J=8.4Hz, 1.8Hz, 1H), 6.87 (d, J=8.9, 2H), 6.10-5.94 (m, 1H), 5.42-5.34 (m, 1H), 5.32-5.19 (m, 1H), 4.47 (d, J=5.2Hz, 2H), 4.05 (s, 2H), 4.02 (d, J=5.8Hz, 2H), 2.67 (s, 3H), 1.49 (s, 9H).

Preparation M (Z)-tert-Butyl N-(4-(2-bromoacetamido)-3-chlorobenzyl)-N'-(3-(4-(allyloxy)phenyl)-5-methylisoxazole-4-carbonyl)carbamimidoylcarbamate

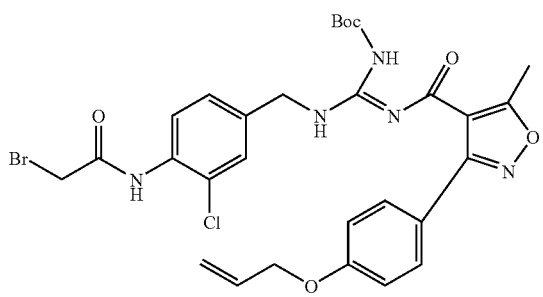

The title compound was prepared from (E)-tert-butyl N-(3-(4-(allyloxy)phenyl)-5-methylisoxazole-4-carbonyl)(methylthio)carbonoimidoyl-carbamate (Preparation F) in analogy to the preparation of (Z)-tert-butyl N-(4-(2-bromoacetamido)-3,5-dichlorobenzyl)-N'-(3-(4-(allyloxy)phenyl)-5-methylisoxazole-4-carbonyl)carbamimidoylcarbamate (Preparation H) from (E)-tert-butyl N-(3-(4-(allyloxy)phenyl)-5-methylisoxazole-4-carbonyl)(methylthio)carbonoimidoyl-carbamate (Preparation F). LCMS (method B) RT 3.81 min., MH+660 (base peak 662). ¹H NMR (500 MHz, CDCl₃) δ 12.17 (s, 1H), 8.92-8.70 (2H), 8.33-8.24 (m, 1H), 7.50 (d, J=8.1Hz, 2H), 7.15 (s, 1H), 7.06 (d, J=8.5Hz, 1H), 6.88 (d, J=8.1, 2H), 6.06-5.95 (m, 1H), 5.42-5.34 (m, 1H), 5.29-5.22 (m, 1H), 4.47 (d, J=5.2Hz, 2H), 4.22 (s, 1H), 4.14 (d, J=5.5Hz, 2H), 4.06 (s, 1H), 2.68 (s, 3H), 1.48 (s, 9H).

Preparation N (Z)-tert-Butyl N-(4-(2-bromoacetamido)benzyl)-N'-(3-(4-(allyloxy)phenyl)-5-methylisoxazole-4-carbonyl)carbamimidoylcarbamate

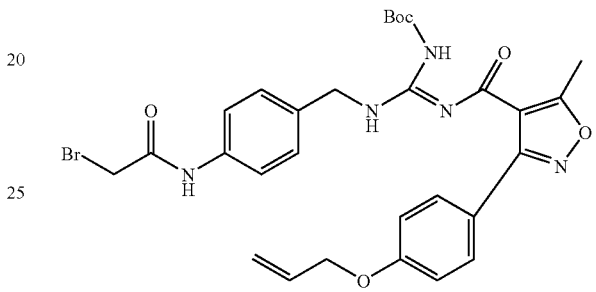

The title compound was prepared from (E)-tert-butyl N-(3-(4-(allyloxy)phenyl)-5-methylisoxazole-4-carbonyl)(methylthio)carbonoimidoylcarbamate (Preparation F) in analogy to the preparation of (Z)-tert-butyl N-(4-(2-bromoacetamido)-3,5-dichlorobenzyl)-N'-(3-(4-(allyloxy)phenyl)-5-methylisoxazole-4-carbonyl)carbamimidoylcarbamate (Preparation H) from (E)-tert-butyl N-(3-(4-(allyloxy)phenyl)-5-methylisoxazole-4-carbonyl)(methylthio)carbonoimidoyl-carbamate (Preparation F). LCMS (method B) RT 3.73 min., MH+626 (base peak 628). ¹H NMR (500 MHz, CDCl₃) δ 12.16 (s, 1H), 8.75 (t, J=5.3Hz, 1 H), 8.27 (s, 1H), 7.59-7.40 (m, 4H), 7.14 (d, J=8.4, 2H), 6.89 (d, J=8.8, 2H), 6.10-5.89 (m, 1H), 5.42-5.32 (m, 1H), 5.29-5.21 (m, 1H), 4.49-4.40 (m, 2H), 4.19 (d, J=5.5Hz, 2H), 4.16 (s, 2H), 2.68 (s, 3H), 1.46 (s, 9H).

SPECIFIC EMBODIMENTS

Example 1

9-Amino-14,30-dichloro-5-methyl-4,24-dioxa-3,8,10,16,19-pentaazatetracyclo-[23.2.2.2$^{12,15}$.0$^{2,6}$]hentriaconta-1(27),2,5,8,12,14,21,25,28,30-decaene-7,17-dione

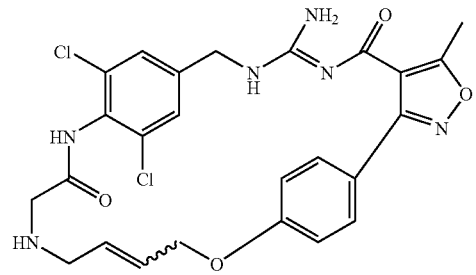

Step 1(A): (Z)-tert-Butyl N-(4-(2-(allylamino)aceta-mido)-3,5-dichlorobenzyl)-N'-(3-(4-(allyloxy)phe-nyl)-5-methylisoxazole-4-carbonyl)carbamimidoyl-carbamate

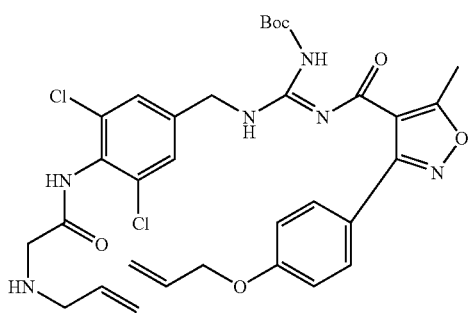

(Z)-tert-Butyl N-(4-(2-bromoacetamido)-3,5-dichlorobenzyl)-N'-(3-(4-(allyloxy)phenyl)-5-methylisoxazole-4-carbonyl)carbamimidoylcarbamate (Preparation H) (150 mg, 0.216 mmol) was dissolved in 4.5 mL of DCM, followed by the addition of allylamine (62 mg, 1.08 mmol) and DIPEA (52 mg, 0.40 mmol). The resulted reaction mixture was stirred at room temperature overnight. Solvent and excessive reagents were evaporated in vacuo to give a crude product, which was used in the next step without purification. LCMS (method B) RT 3.46 min., MH$^+$671.

Step 1(B): tert-Butyl allyl(2-((4-(((((Z)-(((3-(4-(ally-loxy)phenyl)-5-methyl-4-isoxazolyl)carbonyl)imino) ((tert-butoxycarbonyl)amino)methyl)amino)methyl)-2,6-dichlorophenyl)amino)-2-oxoethyl)carbamate

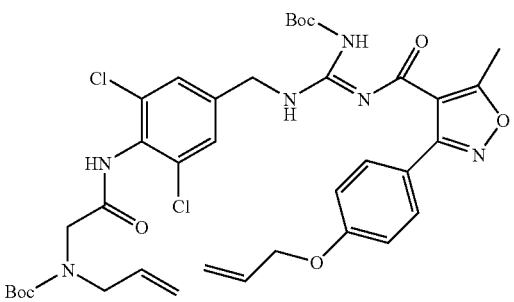

The crude product from Step 1(A) was dissolved in 5 mL of DCM, followed by the addition of di-tert-butyl-dicarbonate (87 mg, 0.4 mmol) and DIPEA (52 mg, 0.40 mmol). The resulted mixture was stirred at room temperature overnight. Solvent was evaporated to give a crude product, which was purified by flash chromatography (EtOAc/DCM, 5:95, Rf 0.15) to give 170 mg (100%).

LCMS (method B) RT 3.88 min., MH$^+$771.

Step 1(C): tert-Butyl 9-((tert-butoxycarbonyl) amino)-14,30-dichloro-5-methyl-7,17-dioxo-4,24-dioxa-3,8,10,16,19-pentaazatetracyclo[23.2.2$^{12,15}$.0$^{2,6}$]-hentriaconta-1(27),2,5,8,12,14,21,25,28,30-decaene-19-carboxylate

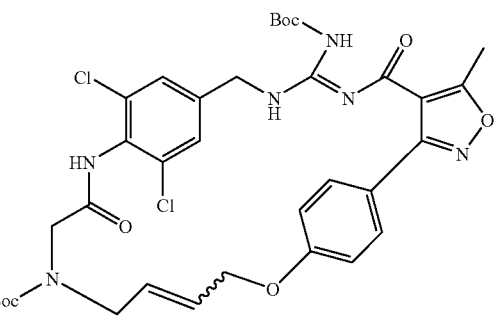

The intermediate (170 mg, 0.216 mmol) from Step 1(B) was dissolved in 35 mL of 1,2-dichloroethane, followed by the addition of Grubbs Catalyst 2$^{nd}$ Generation (40 mg, 0.047 mmol) with 2 mL of 1,2-dichloroethane. The resulted reaction mixture was stirred at 45° C. for 2 hrs. Solvent was evaporated in vacuo to give a crude product, which was purified by flash chromatography (15% EtOAc/DCM, Rf 0.37) to give 85 mg (53%, theoretical yield 161 mg).

LCMS (method B) RT 3.79 min., MH$^+$743.

Step 1(D): 9-Amino-14,30-dichloro-5-methyl-4,24-dioxa-3,8,10,16,19-pentaazatetracyclo[23.2.2$^{12,15.}$0$^{2,6}$]hentriaconta-1(27),2,5,8,12,14,21,25,28,30-decaene-7,17-dione The intermediate (24 mg) from Step 1(C) was dissolved in 2 mL of TFA and DCM mixture (1:1). The resulted solution was stirred at room temperature for 1 h. TFA and DCM were evaporated in vacuo to give a crude product, which was purified by preparative HPLC to give the title compound as a TFA salt (19.9 mg).

LCMS (method B) RT 2.15 min., MH$^+$543.

Example 2

(22E)-9-Amino-14,31-dichloro-5-methyl-4,25-di-oxa-3,8,10,16,19-pentaazatetracyclo[24.2.2$^{12,15}$.0$^{2,6}$] dotriaconta-1(28),2,5,8,12,14,22,26,29,31-decaene-7,17-dione

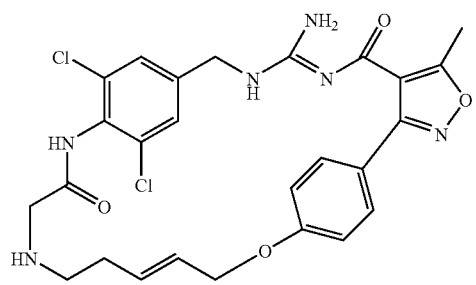

Step 2(A): (Z)-3-(4-(Allyloxy)phenyl)-N-((4-(2-(but-3-enylamino)acetamido)-3,5-dichlorobenzylamino)(tert-butoxycarbonylamino)methylene)-5-methyl-isoxazole-4-carboxamide

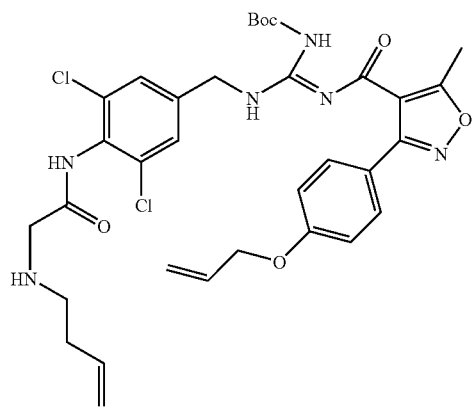

The intermediate was prepared from (Z)-tert-butyl N-(4-(2-bromoacetamido)-3,5-dichlorobenzyl)-N'-(3-(4-(allyloxy)phenyl)-5-methylisoxazole-4-carbonyl)carbamimidoylcarbamate (Preparation H) and with but-3-en-1-amine using the procedure described in Example 1, Step 1(A).

LCMS (method C) RT 2.76 min., MH$^+$685.

Step 2(B): tert-Butyl ((Z)-(((3-(4-(allyloxy)phenyl)-5-methyl-4-isoxazolyl)carbonyl)imino)((4-((N-3-buten-1-yl-N-(tert-butoxycarbonyl)-glycyl)amino)-3,5-dichlorobenzyl)amino)methyl)carbamate

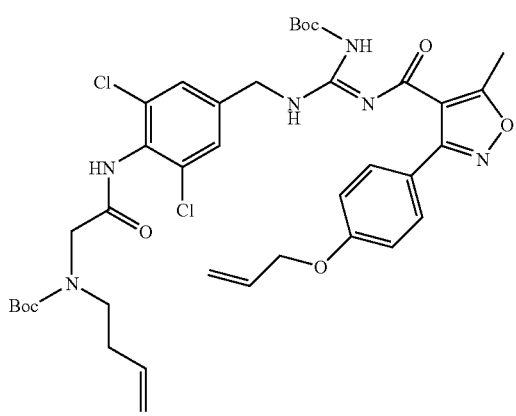

The title intermediate was prepared using the intermediate from Step 2(A) and following the procedure described in Example 1, Step 1(B).

LCMS (method B) RT 3.94 min., MH$^+$785. $^1$H NMR (500 MHz, CDCl$_3$) δ 12.17 (s, 1H), 8.80 (t, J=5.5Hz, 1H), 7.48 (d, J=8.5, 2H), 7.08 (s, 2H), 6.89 (d, J=8.5, 2H), 6.08-5.96 (m, 1H), 5.85-5.70 (m, 1H), 5.43-5.35 (m, 1H), 5.30-5.23 (m, 1H), 5.14-5.01 (m, 2H), 4.49 (d, J=5.2Hz, 2H), 4.08 (d, J=5.8Hz, 2H), 4.04 (s, 2H), 3.44 (br, 2H), 2.69 (s, 3H), 2.37 (br, 2H), 1.50, 1.49 (s, 18H).

Step 2(C): tert-Butyl (22E)-9-((tert-butoxycarbonyl)amino)-14,31-dichloro-5-methyl-7,17-dioxo-4,25-dioxa-3,8,10,16,19-pentaazatetracyclo[24.2.2$^{12,15}$.0$^{2,6}$]-dotriaconta-1(28),2,5,8,12,14,22,26,29,31-decaene-19-carboxylate

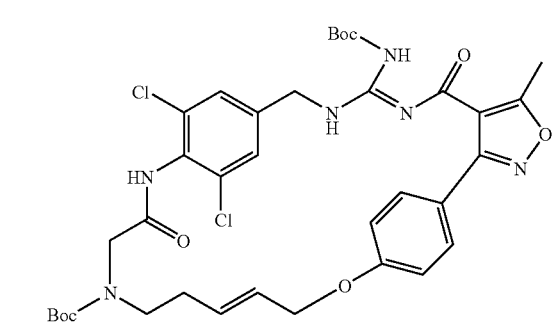

The intermediate was prepared using the intermediate from Step 2(B) and following the procedure described in Example 1, Step 1(C).

LCMS (method B) RT 3.88 min., MH$^+$757. $^1$H NMR (500 MHz, CDCl$_3$) δ 12.17 (s,1H), 8.75 (t, J=5.8Hz, 1H), 8.25 (s, 1H), 7.26 (d, J=8.6Hz, 2H), 6.85 (s, 2 H), 6.53 (d, J=8.6Hz, 2H), 5.99 (br, 1H), 5.91-5.77 (m, 1H), 4.24 (d, J=4.9 Hz, 2H), 4.16-4.06 (m, 2H), 3.99 (s, 2H), 2.66 (s, 5H), 1.54 (s, 9H), 1.52 (s, 9 H).

Step 2(D): (22E)-9-Amino-14,31-dichloro-5-methyl-4,25-dioxa-3,8,10,16,19-pentaazatetracyclo[24.2.2$^{12,15}$.0$^{2,6}$]dotriaconta-1(28),2,5,8,12,14,22,26,29,31-decaene-7,17-dione The title compound was prepared using the intermediate from Step 2(C) by following the procedure described in Example 1, Step 1(D).

LCMS (method B) RT 2.44 min., MH$^+$557. $^1$H NMR (500 MHz, CD$_3$OD) δ 7.59-7.46 (4H), 7.02 (d, J=8.5Hz, 2H), 6.05-5.91 (m, 2H), 4.56 (s, 2H), 4.53 (d, J=4.6Hz, 2H), 4.11 (s, 2H), 3.24 (t, J=6.1Hz, 2H), 2.64 (s, 3H), 2.57-2.50 (m, 2 H).

Example 3

9-Amino-14,32-dichloro-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione

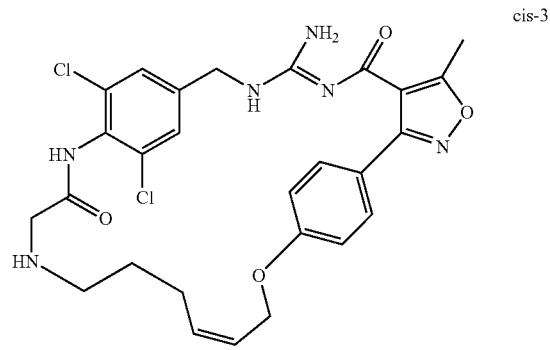

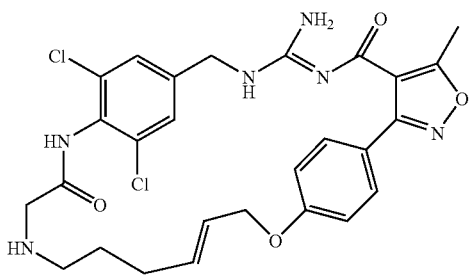

trans-3

Step 3(A): (Z)-3-(4-(Allyloxy)phenyl)-N-((tert-butoxycarbonylamino)(3,5-dichloro-4-(2-(pent-4-enylamino)acetamido)benzylamino)methylene)-5-methylisoxazole-4-carboxamide

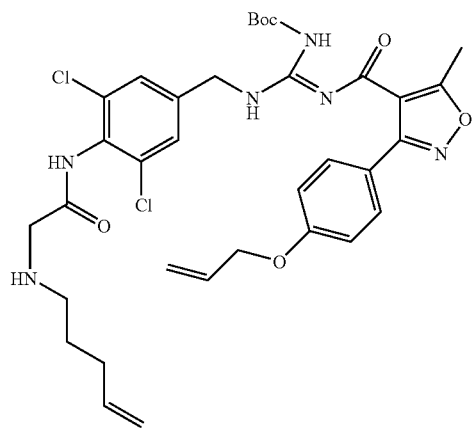

The intermediate was prepared from (Z)-tert-butyl N-(4-(2-bromoacetamido)-3,5-dichlorobenzyl)-N'-(3-(4-(allyloxy)phenyl)-5-methylisoxazole-4-carbonyl)-carbamimidoylcarbamate (Preparation H) and pent-4-en-1-amine by analogy to the procedure described in Example 1, Step 1(A).
LCMS (method C) RT 2.79 min., MH+699.

Step 3(B): tert-Butyl (2-((4-(((((Z)-(((3-(4-(allyloxy)phenyl)-5-methyl-4-isoxazolyl)carbonyl)imino)((tert-butoxycarbonyl)amino)methyl)amino)methyl)-2,6-dichlorophenyl)amino)-2-oxoethyl)4-penten-1-ylcarbamate

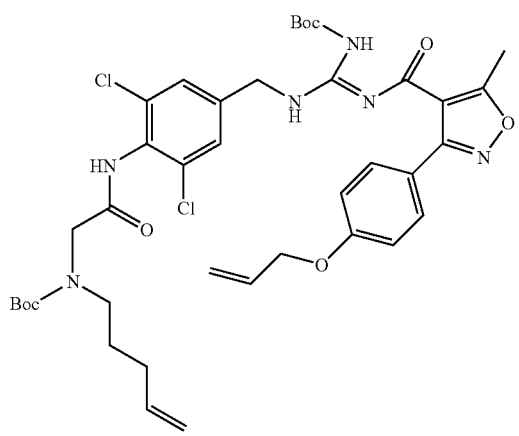

The intermediate was prepared from the intermediate from Step 3(A) by analogy to Example 1, Step 1(B).
LCMS (method B) RT 3.96 min., MH+799.

Step 3(C): tert-Butyl 9-((tert-butoxycarbonyl)amino)-14,32-dichloro-5-methyl-7,17-dioxo-4,26-dioxa-3,8,10,16,19-pentaazatetracyclo[25.2.2.2$^{12,15}$.0$^{2,6}$]-tritriaconta-1(29),2,5,8,12,14,23,27,30,32-decaene-19-carboxylate cis-3C

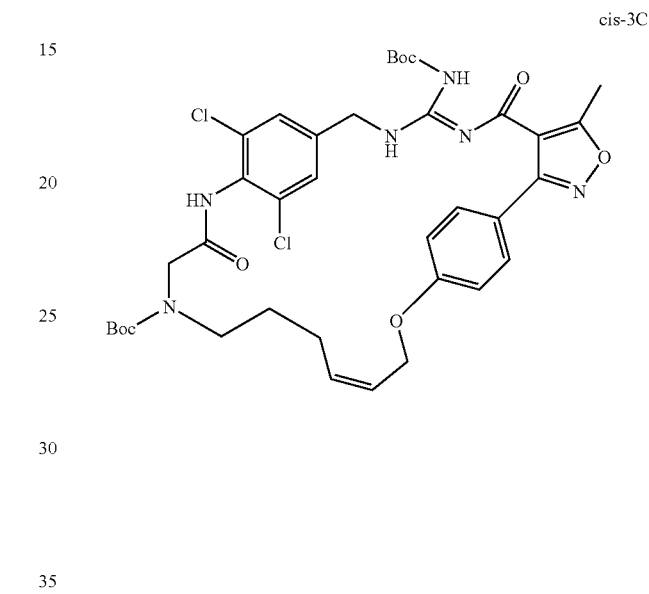

trans-3C

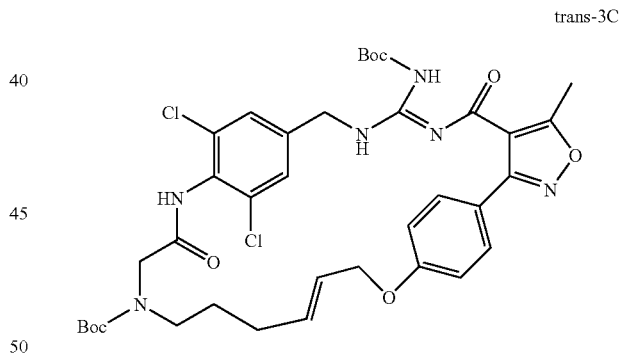

The intermediate (50 mg, 0.063 mmol) from Step 3(B) was dissolved in 15 mL of 1,2-dichloroethane, followed by the addition of Grubbs Catalyst $2^{nd}$ Generation (17 mg, 0.020 mmol) with 1 mL of 1,2-dichloroethane. The resulted reaction mixture was stirred at 40° C. for 2 hrs. Solvent was evaporated in vacuo to give a crude product, which was purified by flash chromatography (15% EtOAc/DCM) to give two compounds, 11 mg of cis-3C (Rf 0.47) and 23 mg of trans-3C (Rf 0.28).

cis-3C: LCMS (method B) RT 3.97 min., MH+771.
trans-3C: LCMS (method B) RT 3.88 min., MH+771.

Step 3(D): 9-Amino-14,32-dichloro-5-methyl-4,26-dioxa-3,8,10,16,19-pentaazatetracyclo[25.2.2.2$^{12,15}$.0$^{2,6}$]tritriaconta-1(29),2,5,8,12,14,23,27,30,32-decaene-7,17-dione The title compounds were prepared from the intermediates from Step 3(C) by analogy to the procedure described in Example 1, Step 1(D).

Cis-3: LCMS (method B) RT 2.49 min., MH$^+$571. $^1$H NMR (500 MHz, CD$_3$OD) δ 7.54-7.46 (4H), 7.01 (d, J=8.5Hz, 2H), 5.85-5.74 (m, 1H), 5.68-5.56 H), 4.64 (d, J=6.1Hz, 2H), 4.61 (s, 2H), 4.14 (s, 2H), 3.12 (t, J=6.9Hz, 2H), 2.64 (s, 3H), 2.35 (q, 2H), 1.87 (m, 2H).

Trans-3: LCMS (method B) RT 2.48 min., MH$^+$571 $^1$H NMR (500 MHz, CD$_3$OD) δ 7.57 (d, J=8.5Hz, 2H), 7.34 (s, 2H), 7.10 (d, J=8.5Hz, 2H), 5.90-5.77 (m, 2H), 4.60 (s, 2H), 4.47 (d, J=3.4Hz, 2H), 4.12 (s, 2H), 3.14 (t, J=8.1Hz, 2H), 2.64 (s, 3H), 2.31 (q, 2H), 1.90 (m, 2H).

Example 4

9-Amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione

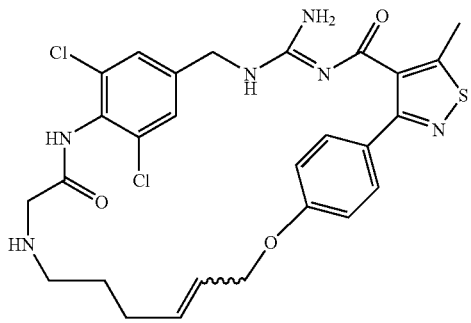

Step 4(A): (Z)-3-(4-(Allyloxy)phenyl)-N-((tert-butoxycarbonylamino)(3,5-dichloro-4-(2-(pent-4-enylamino)acetamido)benzylamino)methylene)-5-methylisothiazole-4-carboxamide

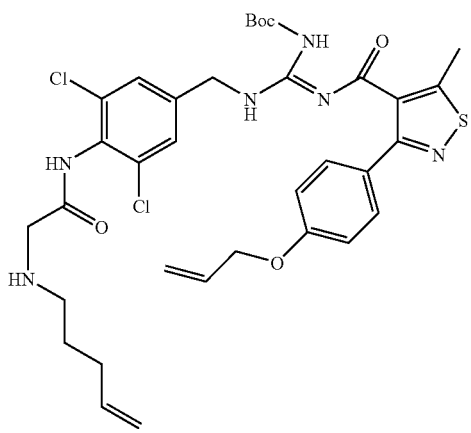

The intermediate was prepared from (Z)-tert-butyl N-(4-(2-bromoacetamido)-3,5-dichlorobenzyl)-N'-(3-(4-(allyloxy)phenyl)-5-methylisothiazole-4-carbonyl)carbamimidoylcarbamate (Preparation K) and pent-4-en-1-amine by analogy to the procedure described in Example 1, Step 1(A).
LCMS (method B) RT 3.15 min., MH$^+$715.

Step 4(B): tert-Butyl (2-((4-((((Z)-(((3-(4-(allyloxy)phenyl)-5-methyl-4-isothiazolyl)carbonyl)imino)((tert-butoxycarbonyl)amino)methyl)amino)-methyl)-2,6-dichlorophenyl)amino)-2-oxoethyl)4-penten-1-ylcarbamate

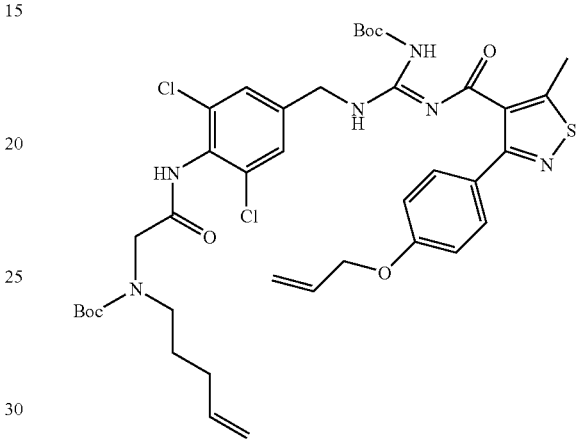

The intermediate was prepared from the intermediate from Step 4(A) by analogy to the procedure described in Example 1, Step 1(B).
LCMS (method C) RT 3.23 min., MH$^+$815.
$^1$H NMR (500 MHz, CDCl$_3$) δ 12.09 (s, 1H), 8.74 (s, 1H), 7.47 (d, J=8.7, 2H), 7.10 (s, 2H), 6.87 (d, J=8.7, 2H), 6.09-5.96 (m, 1H), 5.86-5.72 (m, 1H), 5.45-5.35 (m, 1H), 5.32-5.24 (m, 1H), 5.08-4.92 (m, 2H), 4.49 (d, J=4.9Hz, 2H), 4.02 (s, 2H), 3.97 (d, J=5.5Hz, 2H), 3.35 (s, 2H), 2.66 (s, 3H), 2.11-2.02 (m, 2H), 1.75-1.64 (m, 2H), 1.50 (s, 9H), 1.49 (s, 9H).

Step 4(C): tert-Butyl 9-((tert-butoxycarbonyl)amino)-14,32-dichloro-5-methyl-7,17-dioxo-26-oxa-4-thia-3,8,10,16,19-pentaazatetracyclo[25.2.2.2$^{12,15}$.0$^{2,6}$]-tritriaconta-1(29),2,5,8,12,14,23,27,30,32-decaene-19-carboxylate

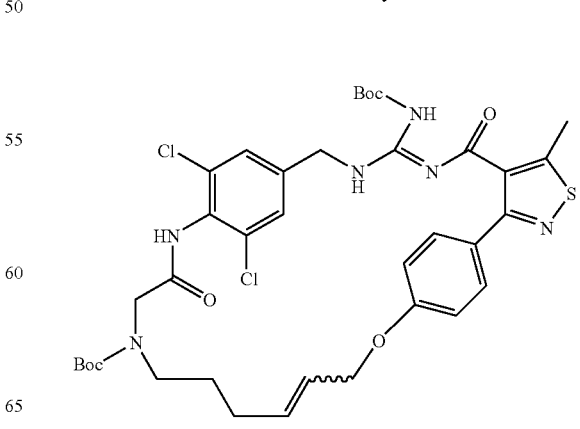

The intermediate (114 mg, 0.140 mmol) from Step 4(B) was dissolved in 45 mL of 1,2-dichloroethane, followed by the addition of Grubbs Catalyst 1st Generation (22 mg, 0.020 mmol) with 1 mL of 1,2-dichloroethane. The resulted reaction mixture was stirred at 70° C. for 6 hrs. (additional 14 mg of Grubbs Catalyst was added 2 hrs. after the initial addition) Solvent was evaporated in vacuo to give a crude product, which was purified by flash chromatography (10% EtOAc/DCM, Rf 0.19) to give 75 mg (68%, theoretical yield 110 mg) of the product, which is a mixture of cis and trans isomers. LCMS (method B) RT 3.78 min., MH$^+$787.8.

Step 4(D): 9-Amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione The title compounds were prepared using the intermediates from Step 4(C) by analogy to the procedure described in Example 1, Step 1(D).

LCMS (method B) RT 2.60 min., MH$^+$587.5. $^1$H NMR (500 MHz, CD$_3$OD) δ 7.60 (minor 7.53) (d, J=8.2Hz, 2H), 7.28 (minor 7.45) (s, 2H), 7.08 (minor 6.98) (d, J=8.2Hz, 2H), 5.91-5.55 (m, 2H), 4.63 (s, 2H), 4.46 (minor 4.61) (s, 2H), 4.12 (minor 4.13) (s, 2H), 3.20-3.06 (m, 2H), 2.70 (minor 2.71) (s, 3H), 2.39-2.25 (m, 2H), 1.99-1.81 (m, 2H).

Example 5

9-Amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,27,30,32-nonaene-7,17-dione

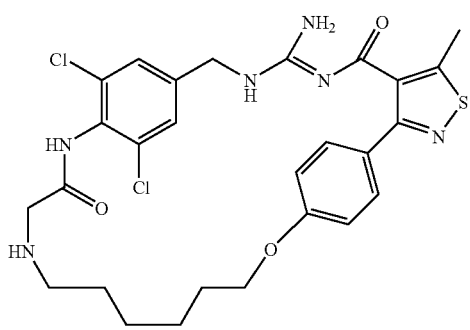

The intermediate (20 mg) from Example 4, Step 4(C) was dissolved in methanol (4 mL), followed by the addition of 10-20 mg of 5% Pd/C. Hydrogen was introduced with a balloon and the reaction mixture was stirred at room temperature for 30 min. (longer reaction time for reaction at larger scale). The reaction mixture was filtered through Celite to remove the catalyst. Solvent was evaporated in vacuo to give a crude product, which was subjected to the protocol described in Example 1, Step 1(D) to yield the title compound.

LCMS (method B) RT 2.62 min., MH$^+$589.3. $^1$H NMR (500 MHz, CD$_3$OD) δ 7.59 (d, J=8.9Hz, 2H), 7.37 (s, 2H), 7.05 (d, J=8.9Hz, 2H), 4.67 (s, 2H) 4.13 (s, 2H), 4.03-3.93 (m, 2H), 3.17 (t, J=7.9Hz, 2H), 2.70 (s, 3H), 1.89-1.72 (m, 4H), 1.62-1.51 (m, 4H).

Example 6

9-Amino-19-benzyl-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione

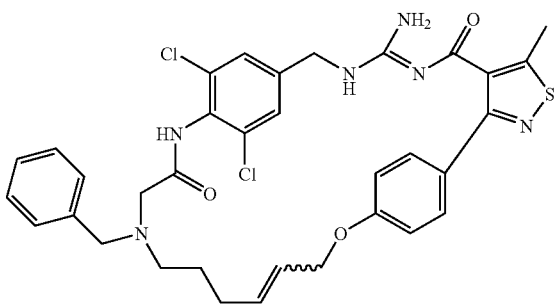

The cis/trans mixture of the title compound of 9-amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione (Example 4) (60 mg), benzaldehyde (24 mg), sodium triacetoxyborohydride (30 mg), trimethyl orthoformate (0.2 mL) and acetic acid (0.1 mL), in 2 mL of DMF was stirred at room temperature for 16 hrs. Ethyl acetate (10 mL) and saturated sodium bicarbonate solution (10 mL) were added. Layers were separated after the mixture was well shaken. The organic layer was dried over anhydrous magnesium sulfate and solvent was evaporated in vacuo to give a crude product, which was purified by preparative HPLC to give 27 mg of the title compound as an inseparable mixture of cis/trans isomers.

LCMS (method B) RT 2.80 min., MH$^+$677 (base peak 679).

Example 7
(24Z)-9-Amino-14,33-dichloro-5-methyl-4,27-dioxa-3,8,10,16,19-pentaazatetracyclo[26.2.2.2$^{12,15}$.0$^{2,6}$] tetratriaconta-1(30),2,5,8,12,14,24,28,31,33-decaene-7,17-dione; and (24E)-9-Amino-14,33-dichloro-5-methyl-4,27-dioxa-3,8,10,16,19-pentaazatetracyclo[26.2.2.2$^{12,5}$.0$^{2,6}$] tetratriaconta-1(30),2,5,8,12,14,24,28,31,33-decaene-7,17-dione;

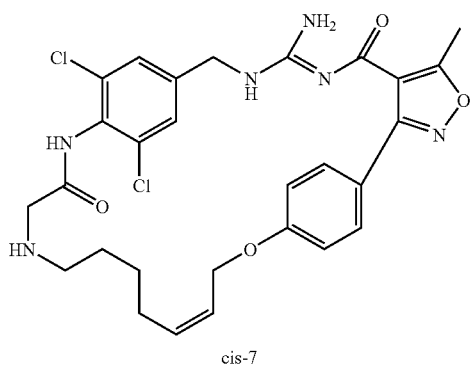

cis-7

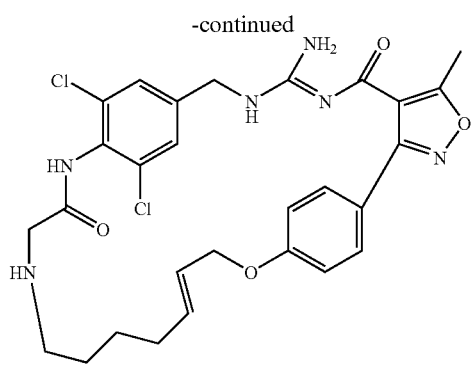

trans-7

Step 7(A): (Z)-3-(4-(Allyloxy)phenyl)-N-((tert-butoxycarbonylamino)(3,5-dichloro-4-(2-(hex-5-enylamino)acetamido)benzylamino)methylene)-5-methylisoxazole-4-carboxamide

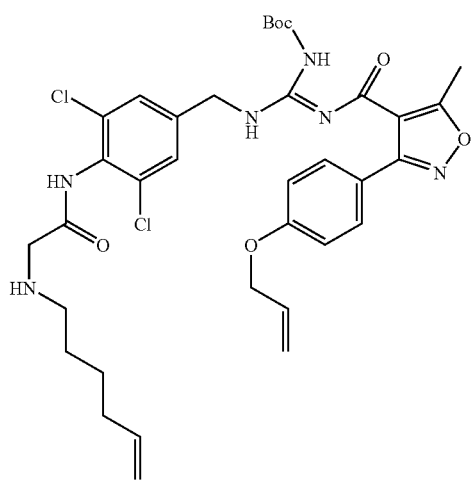

The title intermediate was prepared from (Z)-tert-butyl N-(4-(2-bromoacetamido)-3,5-dichlorobenzyl)-N'-(3-(4-(allyloxy)phenyl)-5-methylisoxazole-4-carbonyl)carbamimidoylcarbamate (Preparation H) and hex-5-en-1-amine by analogy to the procedure described in Example 1, Step 1(A). LCMS (method B) RT 3.57 min., MH$^+$713.

Step 7(B): tert-Butyl (2-((4-(((((Z)-(((3-(4-(allyloxy)phenyl)-5-methyl-4-isoxazolyl)carbonyl)imino)((tert-butoxycarbonyl)amino)methyl)amino)methyl)-2,6-dichlorophenyl)amino)-2-oxoethyl)5-hexen-1-ylcarbamate

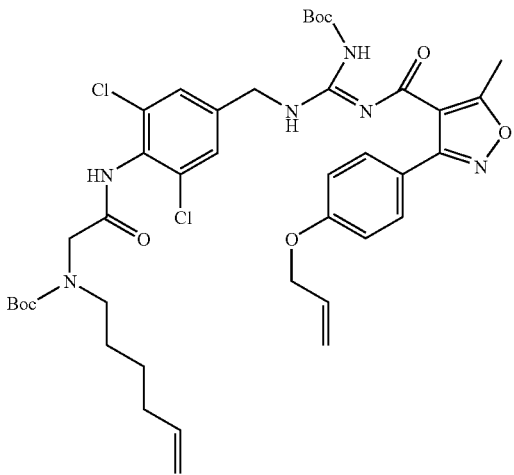

The intermediate was prepared using the intermediate from Step 7(A) by analogy to the procedure described in Example 1, Step 1(B).
LCMS (method B) RT 4.01 min., MH$^+$813.

Step 7(C): tert-Butyl (24Z)-9-((tert-butoxycarbonyl)amino)-14,33-dichloro-5-methyl-7,17-dioxo-4,27-dioxa-3,8,10,16,19-pentaazatetracyclo[26.2.2.2$^{12,15}$.0$^{2,6}$]-tetratriaconta-1(30),2,5,8,12,14,24,28,31,33-decaene-19-carboxylate; and
tert-Butyl (24E)-9-((tert-butoxycarbonyl)amino)-14,33-dichloro-5-methyl-7,17-dioxo-4,27-dioxa-3,8,10,16,19-pentaazatetracyclo[26.2.2.2$^{12,15}$.0$^{2,6}$]tetratriaconta-1(30),2,5,8,12,14,24,28,31,33-decaene-19-carboxylate

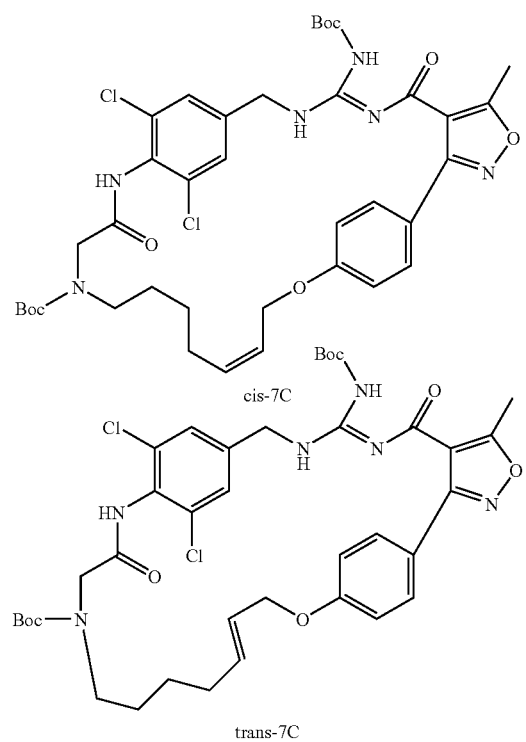

The intermediate (85 mg, 0.104 mmol) from Step 7(B) was dissolved in 27 mL of 1,2-dichloroethane, followed by the addition of Grubbs Catalyst 2$^{nd}$ Generation (6 mg, 0.007 mmol) with 1 mL of 1,2-dichloroethane. The resulting reaction mixture was stirred at 45° C. for 2 hrs. Solvent was evaporated in vacuo to give a crude product, which was purified by flash chromatography (8% EtOAc/DCM) to give two compounds, 8 mg of cis-8C (Rf 0.37) and 45 mg of trans-8C (Rf 0.26).

cis-8C: LCMS (method B) RT 3.991 min., MH$^+$785.
trans-8C: LCMS (method B) RT 3.985 min., MH$^+$785.

Step 7(D): (24Z)-9-Amino-14,33-dichloro-5-methyl-4,27-dioxa-3,8,10,16,19-pentaazatetracyclo[26.2.2.2$^{12,15}$.0$^{2,6}$]tetratriaconta-1(30),2,5,8,12,14,24,28,31,33-decaene-7,17-dione; and
(24E)-9-Amino-14,33-dichloro-5-methyl-4,27-dioxa-3,8,10,16,19-pentaazatetracyclo[26.2.2.2$^{12,15}$.0$^{2,6}$]tetratriaconta-1(30),2,5,8,12,14,24,28,31,33-decaene-7,17-dione The title compounds were prepared from the intermediates from Step 7(C) by analogy to the procedure described in Example 1, Step 1(D).

cis-7: LCMS (method B) RT 2.62 min., MH+585.
trans-7: LCMS (method B) RT 2.63 min., MH+585.

Example 8

(22Z)-9-Amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,22,26,29,31-decaene-7,17-dione; and (22E)-9-Amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,22,26,29,31-decaene-7,17-dione

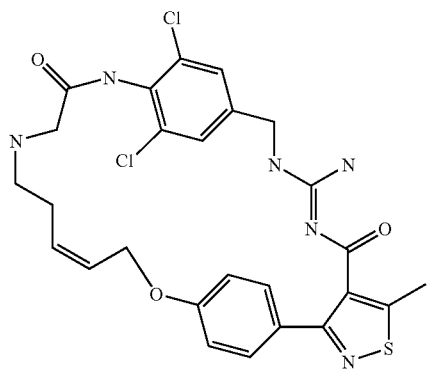

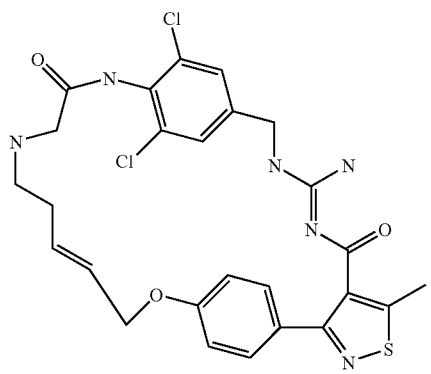

Utilizing (Z)-tert-butyl N-(4-(2-bromoacetamido)-3,5-dichlorobenzyl)-N'-(3-(4-(allyloxy)phenyl)-5-methyl-isothiazole-4-carbonyl)carbamimidoylcarbamate (Preparation K) in place of (Z)-tert-butyl N-(4-(2-bromoacetamido)-3,5-dichlorobenzyl)-N'-(3-(4-(allyloxy)phenyl)-5-methylisoxazole-4-carbonyl)-carbamimidoylcarbamate (Preparation H) and following the synthetic route utilized for Example 2 afforded the title compound as a separable mixture of cis and trans isomers.

cis-8: LCMS (method B) RT 2.17 min., MH+573.
trans-8: LCMS (method B) RT 2.17 min., MH+573.

Example 9

9-Amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,26,29,31-nonaene-7,17-dione

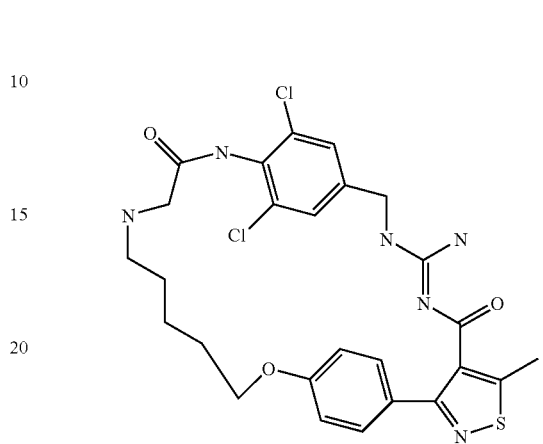

Utilizing a mixture of (22Z)-9-amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,22,26,29,31-decaene-7,17-dione and (22E-9-amino-14,31-dichloro-5-methyl-25-oxa-4-thia-3,8,10,16,19-pentaazatetracyclo[24.2.2.2$^{12,15}$.0$^{2,6}$]-dotriaconta-1(28),2,5,8,12,14,22,26,29,31-decaene-7,17-dione (Example 8) in place of tert-butyl 9-((tert-butoxycarbonyl)amino)-14,32-dichloro-5-methyl-7,17-dioxo-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-19-carboxylate (Example 4, Step (C)), the title compound was synthesized by analogy to Example 5.

LCMS (method B) RT 2.16 min., MH+575.

Example 10

(23Z)-9-Amino-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione; and (23E)-9-Amino-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione

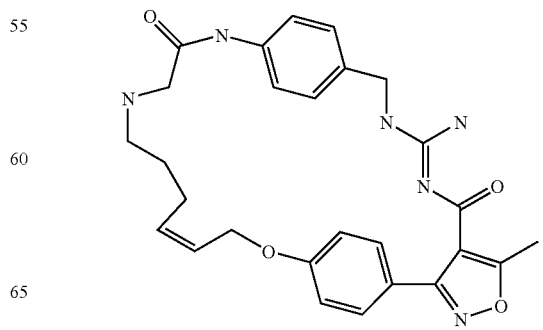

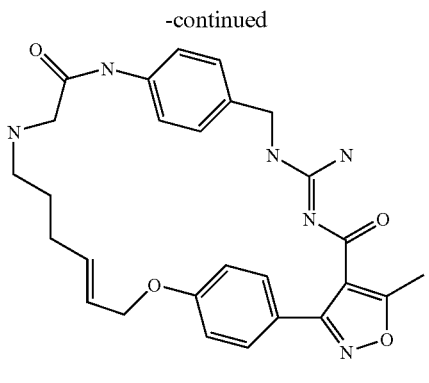

Utilizing (Z)-tert-butyl N-(4-(2-bromoacetamido)-3,5-dichlorobenzyl)-N'-(3-(4-(allyloxy)phenyl)-5-methylisothiazole-4-carbonyl)carbamimidoylcarbamate (Preparation K) in place of (Z)-tert-butyl N-(4-(2-bromoacetamido)-3,5-dichlorobenzyl)-N'-(3-(4-(allyloxy)phenyl)-5-methylisoxazole-4-carbonyl)-carbamimidoylcarbamate (Preparation H) and following the synthetic route utilized for Example 4 afforded the title compound as a separable mixture of cis and trans isomers.

cis-11: LCMS (method B) RT 1.75 min., MH$^+$503.

trans-11: LCMS (method B) RT 1.74 min., MH$^+$503.

Example 11

(23Z)-9-Amino-14-chloro-5-methyl-4,26-dioxa-3,8,10,16,19-pentaazatetracyclo-[25.2.2.2$^{12,5}$.0$^{2,6}$]tritriaconta-1(29),2,5,8,12,14,23,27,30,32-decaene-7,17-dione; and (23E)-9-Amino-14-chloro-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione

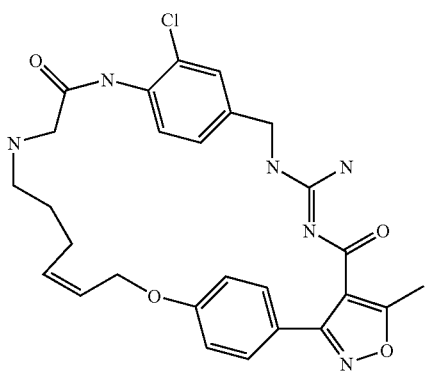

Utilizing (Z)-tert-butyl N-(4-(2-bromoacetamido)-3-chlorobenzyl)-N'-(3-(4-(allyloxy)phenyl)-5-methylisoxazole-4-carbonyl)carbamimidoylcarbamate (Preparation M) in place of (Z)-tert-butyl N-(4-(2-bromoacetamido)-3,5-dichlorobenzyl)-N'-(3-(4-(allyloxy)phenyl)-5-methylisothiazole-4-carbonyl)carbamimidoylcarbamate (Preparation K) and following the synthetic route utilized for Example 4 afforded the title compound as a separable mixture of cis and trans isomers.

cis-12: LCMS (method B) RT 2.43 min., MH$^+$537.

trans-12: LCMS (method B) RT 2.46 min., MH$^+$537.

Example 12

9-Amino-14-chloro-5-methyl-4,26-dioxa-3,8,10,16,19-pentaazatetracyclo-[25.2.2.2$^{12,15}$.0$^{2,6}$]tritriaconta-1(29),2,5,8,12,14,27,30,32-nonaene-7,17-dione

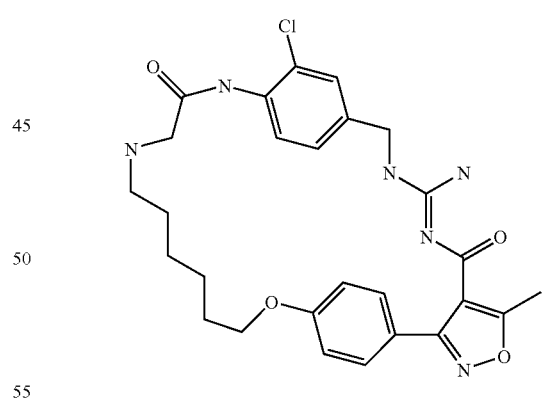

Utilizing a mixture containing (23Z)-9-amino-14-chloro-5-methyl-4,26-dioxa-3,8,10,16,19-pentaazatetracyclo[25.2.2.22$^{12,15}$.0$^{2,6}$]tritriaconta-1 (29),2,5,8,12,14,23,27,30,32-decaene-7,17-dione and (23E)-9-amino-14-chloro-5-methyl-4,26-dioxa-3,8,10,16,19-pentaazatetracyclo[25.2.2.2$^{12,15}$.0$^{2,6}$]tritriaconta-1(29),2,5,8,12,14,23,27,30,32-decaene-7,17-dione (Example 11) in place of Example 4, Step (C), the title compound was synthesized by analogy to Example 5.

LCMS (method B) RT 2.56 min., MH$^+$540.

Example 13

9-Amino-14-chloro-5-methyl-26-oxa-4-thia-3,8,10,16,19-pentaazatetracyclo-[25.2.2.2$^{12,15}$.0$^{2,6}$]tritriaconta-1(29),2,5,8,12,14,23,27,30,32-decaene-7,17-dione

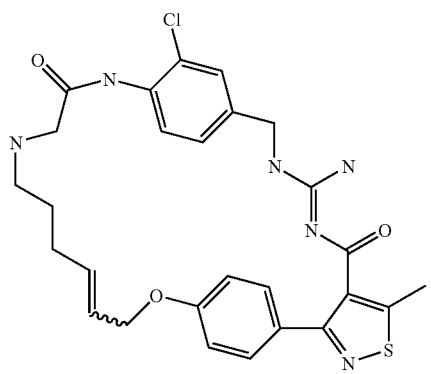

Utilizing (Z)-tert-butyl N-(4-(2-bromoacetamido)-3-chlorobenzyl)-N'-(3-(4-(allyloxy)phenyl)-5-methylisothiazole-4-carbonyl)carbamimidoylcarbamate (Preparation L) in place of (Z)-tert-butyl N-(4-(2-bromoacetamido)-3,5-dichlorobenzyl)-N'-(3-(4-(allyloxy)phenyl)-5-methylisothiazole-4-carbonyl)carbamimidoylcarbamate (Preparation K) and following the synthetic route utilized for Example 4 afforded the title compound as an inseparable mixture of cis and trans isomers.

LCMS (method B) RT 2.16 min., MH$^+$553.

Example 14

9-Amino-14,32-dichloro-5-methyl-4,26-dioxa-3,8,10,16,19-pentaazatetracyclo-[25.2.2.2$^{12,15}$.0$^{2,6}$]tritriaconta-1(29),2,5,8,12,14,27,30,32-nonaene-7,17-dione

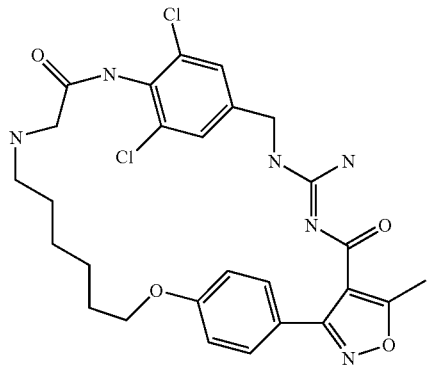

Utilizing a mixture containing (23Z)-9-amino-5-methyl-4,26-dioxa-3,8,10,16,19-pentaazatetracyclo[25.2.2.2$^{12,15}$.0$^{2,6}$] tritriaconta-1 (29),2,5,8,12,14,23,27,30,32-decaene-7,17-dione and (23E-9-amino-5-methyl-4,26-dioxa-3,8,10,16,19-pentaazatetracyclo[25.2.2.2$^{12,15}$.0$^{2,6}$]tritriaconta-1(29),2,5,8,12,14,23,27,30,32-decaene-7,17-dione (Example 10) in place of Example 4, Step (C), the title compound was synthesized by analogy to Example 5.

LCMS (method B) RT 2.59 min., MH$^+$573.

Example 15

9-Amino-14,32-dichloro-5,19-dimethyl-4,26-dioxa-3,8,10,16,19-pentaazatetracyclo[25.2.2.2$^{12,15}$.0$^{2,6}$] tritriaconta-1(29),2,5,8,12,14,23,27,30,32-decaene-7,17-dione

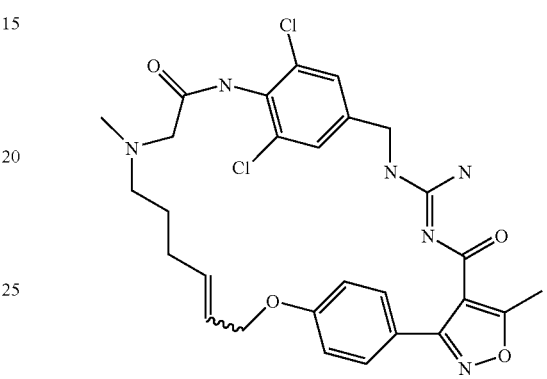

Utilizing formaldehyde in place of benzaldehyde and following the synthetic route utilized for Example 6 afforded the title compound as an inseparable mixture of cis and trans isomers.

LCMS (method B) RT 2.48 min., MH$^+$585.

Example 16

9-Amino-14,32-dichloro-5-methyl-19-(3,3,3-trifluoropropyl)-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione

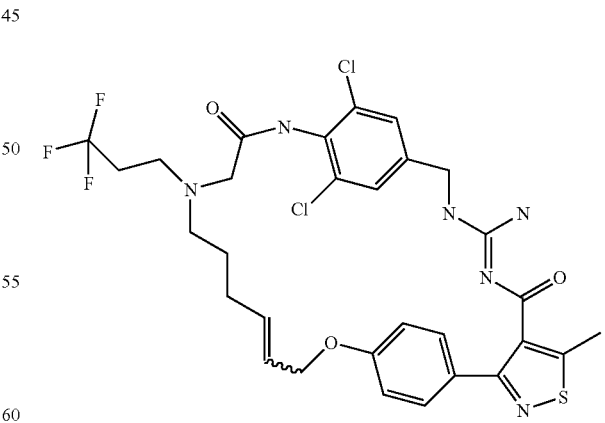

Utilizing 2,2,2-trifluoropropionaldehyde in place of benzaldehyde and following the synthetic route utilized for Example 6 afforded the title compound as an inseparable mixture of cis and trans isomers.

LCMS (method B) RT 2.42 min., MH$^+$683.

Biological Methods

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in Drosophila melanogaster S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., "Characterization of recombinant, soluble beta-secretase from an insect cell expression system." *Mol. Pharmacol.* 2001, 59: 619-626]. Similar strategies for expressing and purifying various forms of BACE in bacterial, mammalian and other cell types would be known to one skilled in the art. A preferred method for determining the potency of a test compound in binding to the BACE enzyme is by monitoring the displacement of a suitable radioligand.

Radioligand displacement assays with a radiolabeled BACE inhibitor (WO 2004 013098, compound 3, where the methoxy group is substituted for $C(^3H)_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 µg/ml penicillin, 10 µg/ml streptomycin, 3 µg/ml puromycin, 100 nM methotrexate, and 10% fetal bovine serum (Invitrogen, Carlsbad, Calif.), harvested, and resuspended at $2 \times 10^8$ cells per 10 ml of lysis buffer consisting of 50 mM HEPES pH 7.0 containing a protease inhibitor cocktail of AEBSF 104 µM, aprotinin 80 nM, leupeptin 2 µM, bestatin 4 µM, pepstatin A 1.5 µM, and E-64 1.4 µM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at −70° C. Immediately before carrying out a binding assay, an aliquot of cell homogenate was thawed and diluted to a concentration of 100 µg/ml in assay buffer consisting of 50 mM HEPES pH 5.0 and 0.1% CHAPSO. Assays were initiated in polypropylene 96-well plates (Costar, Cambridge, Mass.) by the addition of 200 µl of cell homogenate to 50 µl of assay buffer containing 1 nM radioligand (WO 2004 013098, compound 3, where the methoxy group is substituted for $C(^3H)_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of $IC_{50}$ values calculated using XLfit (IDBS, Guildford, UK).

ABBREVIATIONS

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

TABLE 1

| Example No. | Activity Rating[a] |
| --- | --- |
| 1 | + |
| 2 | + |
| 3 | ++ |
| 4 | ++ |
| 5 | ++ |
| 6 | ++ |
| 7 | +++ |
| 8 | +++ |
| 9 | +++ |
| 10 | +++ |
| 11 | +++ |

[a]Activity based on $IC_{50}$ values:
+++ = <5 nM
++ = 5-50 nM
+ = >50 nM

In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA,* 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature,* 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of Aβ generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for Aβ quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry,* 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the determination of Aβ reduction by a β-secretase inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

Dosage and Formulation

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixtures. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of the Formula (I); or a stereoisomer thereof

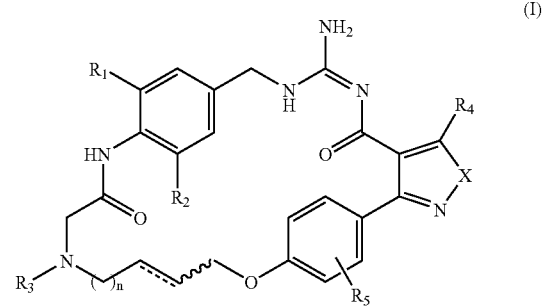

wherein
$\equiv$ represents a single or double bond;
$R_1$ and $R_2$ are independently hydrogen, halogen, $C_{1-4}$alkyl or $CF_3$;
$R_3$ is hydrogen, $C_{1-4}$alkyl, fluoro $C_{1-4}$alkyl, $CF_3$ or benzyl;
$R_4$ is hydrogen, $C_{1-4}$alkyl or phenyl in which each is optionally substituted with halogen, $C_{1-4}$alkyl or $C_{1-4}$alkoxy;
$R_5$ is hydrogen, halogen, $CF_3$, OH, $NH_2$, $C_{1-4}$alkyl or $C_{1-4}$alkoxy;
n is an integer of 1, 2, 3 or 4; and
X is O or S;
or a nontoxic pharmaceutically acceptable salt thereof.

2. The compound of claim 1 wherein $\equiv$ represents a single or double bond; $R_1$ and $R_2$ are halogen; $R_3$ is hydrogen; $R_4$ is hydrogen or $C_{1-4}$alkyl; $R_5$ is hydrogen or halogen; n is an integer of 2 or 3 and X is O or S; or a nontoxic pharmaceutically acceptable salt thereof.

3. The compound of claim 2 wherein $\equiv$ represents a single or double bond; $R_1$ and $R_2$ are chloro; $R_3$ is hydrogen; $R_4$ is methyl; $R_5$ is hydrogen; n is an integer of 2 or 3 and X is O or S; or a nontoxic pharmaceutically acceptable salt thereof.

4. The compound of claim 1 selected from the group consisting of:

- 9-Amino-14,30-dichloro-5-methyl-4,24-dioxa-3,8,10,16,19-pentaazatetracyclo-[23.2.2.2$^{12,15}$.0$^{2,6}$]hentriaconta-1(27), 2,5,8,12,14,21,25,28,30-decaene-7,17-dione;
- (22E)-9-Amino-14,31-dichloro-5-methyl-4,25-dioxa-3,8,10,16,19-pentaazatetracyclo[24.2.2.2$^{12,15}$.0$^{2,6}$]dotriaconta-1(28),2,5,8,12,14,22,26,29,31-decaene-7,17-dione;
- 9-Amino-14,32-dichloro-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- 9-Amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione;
- 9-Amino-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,27,30,32-nonaene-7,17-dione;
- 9-Amino-19-benzyl-14,32-dichloro-5-methyl-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione;
- (24Z)-9-Amino-14,33-dichloro-5-methyl-4,27-dioxa-3,8,10,16,19-pentaazatetracyclo[26.2.2.2$^{12,15}$.0$^{2,6}$]tetratriaconta-1(30)2,5,8,12,14,24,28,31,33-decaene-7,17-dione;
- (24E)-9-Amino-14,33-dichloro-5-methyl-4,27-dioxa-3,8,10,16,19-pentaazatetracyclo[26.2.2.2$^{12,15}$.0$^{2,6}$]tetratriaconta-1(30)2,5,8,12,14,24,28,31,33-decaene-7,17-dione;
- (22Z)-9-Amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,22,26,29,31-decaene-7,17-dione;
- (22E)-9-Amino-14,31-dichloro-5-methyl-25-oxa-4-thia-3,8,10,16,19-pentaazatetracyclo[24.2.2.2$^{12,15}$.0$^{2,6}$]dotriaconta-1(28),2,5,8,12,14,22,26,29,31-decaene-7,17-dione;
- 9-Amino-14,31-dichloro-5-methyl-25-oxa-4-thia-3,8,10,16,1,9-pentaazatetracyclo[24.2.2.2$^{12,15}$.0$^{2,6}$]dotriaconta-1(28),2,5,8,12,14,26,29,31-nonaene-7,17-dione;
- (23Z)-9-Amino-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- (23E)-9-Amino-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- (23Z)-9-Amino-14-chloro-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- (23E)-9-Amino-14-chloro-5-methyl-4,26-dioxa-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- 9-Amino-14-chloro-5-methyl-4,26-dioxa-3,8,10,16,19-pentaazatetracyclo-[25.2.2.2$^{12,15}$.0$^{2,6}$]tritriaconta-1(29),2,5,8,12,14,27,30,32-nonaene-7,17-dione;
- 9-Amino-14-chloro-5-methyl-26-oxa-4-thia-3,8,10,16,19-pentaazatetracyclo-[25.2.2.2$^{12,15}$.0$^{2,6}$]tritriaconta-1(29),2,5,8,12,14,23,27,30,32-decaene-7,17-dione;
- 9-Amino-14,32-dichloro-5-methyl-4,26-dioxa-3,8,10,16,19-pentaazatetracyclo-[25.2.2.2$^{12,15}$.0$^{2,6}$]tritriaconta-1(29),2,5,8,12,14,27,30,32-nonaene-7,17-dione;
- 9-Amino-14,32-dichloro-5,19-dimethyl-4,26-dioxa-3,8,10,16,19-pentaazatetracyclo[25.2.2.2$^{12,15}$.0$^{2,6}$]tritriaconta-1(29),2,5,8,12,14,23,27,30,32-decaene-7,17-dione; and
- 9-Amino-14,32-dichloro-5-methyl-19-(3,3,3-trifluoropropyl)-26-oxa-4-thia-3,8,10,16,19-pentaazatetracyclo[25.2.2.2$^{12,15}$.0$^{2,6}$]tritriaconta-1(29),2,5,8,12,14,23,27,30,32-decaene-7,17-dione;

or a nontoxic pharmaceutically acceptable salt thereof.

5. A pharmaceutical composition comprising a therapeutically effective amount of a compound of claim 1 in association with a pharmaceutically acceptable adjuvant, carrier or diluent.

* * * * *